United States Patent
Chen et al.

(10) Patent No.: US 12,138,070 B2
(45) Date of Patent: Nov. 12, 2024

(54) GAS SENSOR

(71) Applicants: Corning Incorporated, Corning, NY (US); National Yang Ming Chiao Tung University, Hsin-Chu (TW)

(72) Inventors: Chang-Chiang Chen, Zhudong Township (TW); Mingqian He, Horseheads, NY (US); Yang Li, Shanghai (CN); Hsin-Fei Meng, Hsinchu (TW); Hsiao-Wen Zan, Hsinchu (TW)

(73) Assignees: CORNING INCORPORATED, Corning, NY (US); NATIONAL YANG MING CHIAO TUNG UNIVERSITY, Hsin-Chu (TW)

( * ) Notice: Subject to any disclaimer, the term of this patent is extended or adjusted under 35 U.S.C. 154(b) by 632 days.

(21) Appl. No.: 17/389,765

(22) Filed: Jul. 30, 2021

(65) Prior Publication Data
US 2022/0031228 A1    Feb. 3, 2022

(30) Foreign Application Priority Data
Jul. 31, 2020    (CN) .......................... 202010760067.0

(51) Int. Cl.
*A61B 5/00*    (2006.01)
*H10K 85/10*    (2023.01)

(52) U.S. Cl.
CPC ............ *A61B 5/441* (2013.01); *H10K 85/113* (2023.02)

(58) Field of Classification Search
CPC . G01N 27/4141; H10K 10/484; H10K 85/113
See application file for complete search history.

(56) References Cited

U.S. PATENT DOCUMENTS

| | | | |
|---|---|---|---|
| 7,692,269 B2 | 4/2010 | Meng et al. |
| 7,705,108 B2 | 4/2010 | He |
| 7,772,079 B2 | 8/2010 | Meng et al. |
| 7,791,068 B2 | 9/2010 | Meng et al. |
| 7,838,623 B2 | 11/2010 | He |
| 7,893,191 B2 | 2/2011 | He |
| 8,258,554 B2 | 9/2012 | Meng et al. |
| 8,389,669 B2 | 3/2013 | He |

(Continued)

OTHER PUBLICATIONS

Modulated gas sensor based on vertical organic diode with blended channel for ppb-regime detection, Sensors and Actuators B: Chemical, 2016, 230, 223-230, Chuang et al. (Year: 2016).*

(Continued)

*Primary Examiner* — Mayla Gonzalez Ramos
(74) *Attorney, Agent, or Firm* — Travis B. Gasa; Russell S. Magaziner

(57) ABSTRACT

A device for analyzing gas emitted from skin includes: an enclosure for collecting the gas emitted from skin, the enclosure having: an inlet through which a carrier gas is flown; and an outlet through which the carrier gas and the gas emitted from skin is flown into a vertical gas sensor, such that the vertical gas sensor has: a substrate; a collector layer; an emitter layer positively biased relative to the collector; a metal grid with a metal layer having openings, the metal grid located in between, but not in direct contact with, the collector and emitter; and an organic semiconductor (OSC) layer located in between the collector and emitter.

19 Claims, 9 Drawing Sheets

(56) References Cited

U.S. PATENT DOCUMENTS

| | | | |
|---|---|---|---|
| 8,624,232 | B2 | 1/2014 | Sonar et al. |
| 9,331,294 | B2 | 5/2016 | Zan et al. |
| 2008/0128681 | A1* | 6/2008 | Meng ............ H10K 10/00 257/E51.001 |
| 2009/0230383 | A1 | 9/2009 | Meng et al. |
| 2011/0284949 | A1 | 11/2011 | Meng et al. |
| 2014/0045297 | A1 | 2/2014 | Meng et al. |
| 2016/0222167 | A1* | 8/2016 | He ................ C08G 61/124 |
| 2020/0217816 | A1 | 7/2020 | He et al. |
| 2020/0220084 | A1 | 7/2020 | He et al. |

OTHER PUBLICATIONS

Agapiou et al., "Analysis of volatile organic compounds released from the decay of surrogate human models simulating victims of collapsed buildings by thermal desorption—comprehensive two-dimensional gas chromatography—time of flight mass spectrometry", Analytica Chimica ACTA, vol. 883, 2015, pp. 99-108.

Bevc et al., "Measurement of breath ammonia for detection of patients with chronic kidney disease", Jun. 2017, Clinical Nephrology, vol. 88 (13) p. S14-S17.

Chuang et al, "Organic Gas Sensor with an Improved Lifetime for Detecting Breath Ammonia in Hemodialysis Patients", 2017, ACS Sensors, vol. 2 (12), pp. 1788-1795.

Haze et al. "2-Nonenal Newly Found in Human Body Odor Tends to Increase with Aging", Apr. 2001, Journal of Investigative Dermatology, vol. 116 (4), pp. 520-524.

He Jian-cheng et al., "Method for Predicting Clinical State of Disease Based on Information Technology on Diagnosis in Chinese Medicine", 2008, 2008 IEEE International Symposium on it in Medicine and Education, vol. 1 and 2, Proceedings, pp. 583-586.

Saasa et al., "Blood Ketone Bodies and Breath Acetone Analysis and Their Correlations in Type 2 Diabetes Mellitus", 2019, Diagnostics, vol. 9 (4), No. 224 pp. 10.

Shang-Yu Yu et al, "A Versatile Method to Enhance the Operational Current of Air-Stable Organic Gas Sensor for Monitoring of Breath Ammonia in Hemodialysis Patients", Mar. 20, 20192, ACS Sensors, vol. 4 (4), pp. 1023-1031.

Tiele et al., "Breath-based non-invasive diagnosis of Alzheimer's disease: a pilot study", 2020, Journal of breath research, vol. 14 (2), No. 026003, pp. 10.

Zan et al., Room-temperature-operated sensitive hybrid gas sensor-based on amorphous indium gallium zinc oxide thin-film transistors—Applied Physics Letters, 98, 253503, 2011, pp. 3.

Zhang et al., "Diagnostic value of fractional exhaled nitric oxide in cough-variant asthma: an updated metaanalysis", Journal of Asthma, vol. 57 (3), 2020, pp. 335-342.

\* cited by examiner

GAS SENSOR

This application claims the benefit of priority under 35 U.S.C. § 119 of Chinese Patent Application Serial No. 202010760067.0, filed on Jul. 31, 2020, the content of which is relied upon and incorporated herein by reference in its entirety.

BACKGROUND

1. Field

This disclosure relates to high-current organic thin film transistor (OTFT) devices with vertically-designed structures and donor-acceptor-based organic semiconductor (OSC) materials, along with methods for making such devices, and uses thereof.

2. Technical Background

Interest in organic electronics has led to research on OSC devices such as organic light-emitting diodes (OLEDs), organic field-effect transistors (OFETs), organic chemical sensors, and polymer solar cells. Organic semiconductors may substantially reduce cost of manufacturing over their inorganic (e.g., silicon) counterparts since they can be deposited from solution, as this enables fast, large-area fabrication routes such as spin-coating, ink-jet printing, gravure printing, transfer printing, etc. and could have applications in smart cards, security tags, low cost sensors, and as switching elements in the backplane of flat panel displays.

A key component of flexible electronics is the field effect transistor (FET), a horizontal device with source and drain electrodes on the same plane. In the "off" state, there is no charge carrier channel accumulation between source and drain electrodes in the FET. In the "on" state, current flows between the source and drain electrodes and is controlled by a gate voltage applied to the gate electrode. Such devices are usually operated in an accumulation mode, where the gate bias induces a channel of charge carriers at the insulator-semiconductor interface.

For OFETs, two parameters used to characterize performance are current ratio between the on and off states (on/off ratio) and field-effect mobility. Traditional OFETs often suffer from low current output because of intrinsically low carrier mobility due to weak wavefunction overlap between the molecules and disorders in the thin film. The low mobility limits operating frequency to under 100 kHz. Another problem is that current OFETs tend to be unstable due to thin conduction channels (e.g., confined to a few monolayers at the semiconductor-dielectric interface) such that any adsorbed oxygen, moisture, or other chemicals can have deleterious effects on transistor characteristics. Desired current outputs often require operating OFETs at voltages greater than 20V. Research efforts have been made to improve performance of FETs by increasing mobility, reducing gate dielectrics thickness, and/or reducing channel lengths.

This disclosure presents improved OTFT devices having high relative current density at low voltages.

SUMMARY

In some embodiments, a device for analyzing gas emitted from skin, comprises: an enclosure for collecting the gas emitted from skin, the enclosure comprising: an inlet through which a carrier gas is flown; and an outlet through which the carrier gas and the gas emitted from skin is flown into a vertical gas sensor, wherein the vertical gas sensor comprises: a substrate; a collector layer; an emitter layer positively biased relative to the collector; a metal grid comprising a metal layer having openings, the metal grid located in between, but not in direct contact with, the collector and emitter; and an organic semiconductor (OSC) layer located in between the collector and emitter.

In one aspect, which is combinable with any of the other aspects or embodiments, each of the openings has a length along its longest dimension of from about 50 nm to about 800 nm. In one aspect, which is combinable with any of the other aspects or embodiments, the length along its longest dimension is from 200 nm to 500 nm. In one aspect, which is combinable with any of the other aspects or embodiments, the vertical gas sensor further comprises: an insulating layer positioned between the emitter layer and the metal grid.

In one aspect, which is combinable with any of the other aspects or embodiments, the insulating layer is polyvinylpyrrolidone (PVP). In one aspect, which is combinable with any of the other aspects or embodiments, at least the insulating layer and the emitter layer are patterned to form vertical nano-channels configured to adsorb the gas emitted from skin. In one aspect, which is combinable with any of the other aspects or embodiments, the OSC layer is disposed in the vertical nano-channels. In one aspect, which is combinable with any of the other aspects or embodiments, the OSC layer comprises soluble OSC small molecules. In one aspect, which is combinable with any of the other aspects or embodiments, the OSC small molecules include at least one of the structures exemplified in Table 5.

In one aspect, which is combinable with any of the other aspects or embodiments, the OSC layer comprises: an OSC polymer with the structure:

(I)

wherein each D is an independently selected conjugated electron donating aromatic or heteroaromatic group having from 5 to 50 backbone atoms and each D group is optionally substituted with one or more electron donating substituents or electron withdrawing substituents, provided that even when substituted the electronic character of each D is electron donating; each A is an independently selected conjugated electron accepting aromatic or heteroaromatic group having from 5 to 50 backbone atoms or an ethenylene group substituted with one or two electron withdrawing substituents, each A being optionally substituted with one or more electron donating substituents or electron withdrawing substituents provided that even when substituted the electronic character of each A is electron accepting; each of a and b is an integer from 1 to 4, and n is an integer from 2 to 10,000.

In one aspect, which is combinable with any of the other aspects or embodiments, each D is independently one of the structures exemplified in Table 1. In one aspect, which is combinable with any of the other aspects or embodiments, each A is independently one of the structures exemplified in Table 2. In one aspect, which is combinable with any of the other aspects or embodiments, one or more of $R_1$, $R_2$, $R_3$, $R_4$, and $R_6$ is an optionally substituted $C_{15}$-$C_{35}$ alkyl. In one aspect, which is combinable with any of the other aspects or embodiments, one or more of $R_1$, $R_2$, $R_3$, or $R_4$ is an optionally substituted $C_{15}$-$C_{35}$ alkyl having at least one branching point. In one aspect, which is combinable with any of the other aspects or embodiments, one or more of $R_1$, $R_2$, or $R_3$ can be optionally substituted $C_{15}$-$C_{35}$ alkyl. In one aspect, which is combinable with any of the other aspects or embodiments, each $R_1$ or $R_2$ is independently an optionally substituted $C_{15}$-$C_{35}$ alkyl. In one aspect, which is combinable with any of the other aspects or embodiments, each $R_1$ or $R_2$ is independently an optionally substituted $C_{15}$-$C_{35}$ alkyl having at least one branching point. In one aspect, which is combinable with any of the other aspects or embodiments, each $R_1$ or $R_2$ is independently an optionally substituted $C_{15}$-$C_{35}$ alkyl having at least one branching point, where the branching point is at least 4 carbons from the base molecule.

In one aspect, which is combinable with any of the other aspects or embodiments, the OSC layer comprises an OSC polymer including at least one of the structures exemplified in Table 4. In one aspect, which is combinable with any of the other aspects or embodiments, the collector layer comprises Al, Au, Ag, Pt, Cu, stainless steel, oxides thereof, alloys thereof or combinations thereof. In one aspect, which is combinable with any of the other aspects or embodiments, the emitter layer comprises at least one of: a transparent conductive oxide, an organic polymer, or a combination thereof.

In some embodiments, a gas sensor for analyzing gas emitted from skin, comprises: a substrate; a collector layer; an emitter layer positively biased relative to the collector; a metal grid comprising a metal layer having openings, the metal grid located in between, but not in direct contact with, the collector and emitter; and an organic semiconductor (OSC) layer located in between the collector and emitter.

Additional features and advantages will be set forth in the detailed description which follows, and in part will be readily apparent to those skilled in the art from the description or recognized by practicing the embodiments as described in the written description and claims hereof, as well as in the appended drawings.

It is to be understood that both the foregoing general description and the following detailed description are merely exemplary and are intended to provide an overview or framework for understanding the nature and character of the invention.

BRIEF DESCRIPTION OF THE DRAWINGS

The accompanying drawings are included to provide a further understanding of the description and are incorporated in and constitute a part of this specification. The drawings are not necessarily to scale, and sizes of various elements may be distorted for clarity. The drawings illustrate one or more embodiment(s) and together with the description serve to explain the principles and operation of the embodiments.

DETAILED DESCRIPTION

Figure 1:
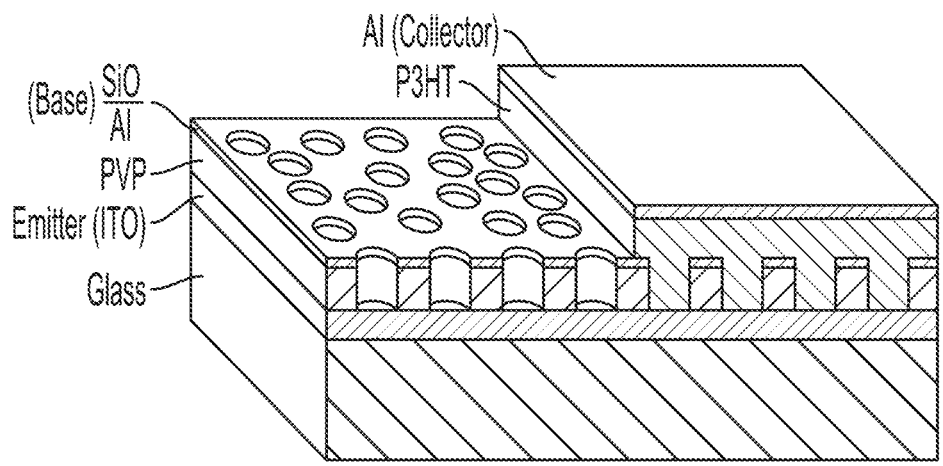
FIG. 1 describes an embodied device design for an organic polymer-based vertical transistor, according to some embodiments.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

"Optional" or "optionally" means that the subsequently described event or circumstance may or cannot occur, and that the description includes instances where the event or circumstance occurs and instances where it does not.

Where a range of numerical values is recited herein, comprising upper and lower values, unless otherwise stated in specific circumstances, the range is intended to include the endpoints thereof, and all integers and fractions within the range. It is not intended that the scope of the claims be limited to the specific values recited when defining a range. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed.

When the term "about" is used in describing a value or an end-point of a range, the disclosure should be understood to include the specific value or end-point referred to. When a numerical value or end-point of a range does not recite "about," the numerical value or end-point of a range is intended to include two embodiments: one modified by "about," and one not modified by "about." It will be further understood that the endpoints of each of the ranges are significant both in relation to the other endpoint, and independently of the other endpoint.

The term 'arylalkene' refers to an alkene group that is directly bonded to an aromatic group.

The term "alkyl group" refers to a monoradical branched or unbranched saturated hydrocarbon chain having 1 to 40 carbon atoms. This term is exemplified by groups such as methyl, ethyl, n-propyl, isopropyl, n-butyl, isobutyl, t-butyl, pentyl, n-hexyl, n-heptyl, n-octyl, n-decyl, or tetradecyl, and the like. The alkyl group can be substituted or unsubstituted.

The term "substituted alkyl group" refers to: (1) an alkyl group as defined above, having 1, 2, 3, 4 or 5 substituents, typically 1 to 3 substituents, selected from the group consisting of alkenyl, alkynyl, alkoxy, aralkyl, aldehyde, cycloalkyl, cycloalkenyl, acyl, acylamino, acyl halide, acyloxy, amino, aminocarbonyl, alkoxycarbonylamino, azido, cyano, halogen, hydroxy, keto, thiocarbonyl, carboxy, carboxyalkyl, arylthiol, ester, heteroarylthio, heterocyclylthio, hydroxyl, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl, thioalkyl, vinyl ether. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkyl group as defined above that is interrupted by 1-10 atoms independently chosen from oxygen, sulfur and NR$_a$, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R$_{SO}$, in which R$_{SO}$ is alkyl, aryl, or heteroaryl and n is 0, 1 or 2; or (3) an alkyl group as defined above that has both 1, 2, 3, 4 or 5 substituents as defined above and is also interrupted by 1-10 atoms as defined above. For example, the alkyl groups can be an alkyl hydroxy group, where any of the hydrogen atoms of the alkyl group are substituted with a hydroxyl group.

The term "alkyl group" as defined herein also includes cycloalkyl groups. The term "cycloalkyl group" as used herein is a non-aromatic carbon-based ring (i.e., carbocyclic) composed of at least three carbon atoms, and in some embodiments from three to 20 carbon atoms, having a single cyclic ring or multiple condensed rings. Examples of single ring cycloalkyl groups include, but are not limited to, cyclopropyl, cyclobutyl, cyclopentyl, cyclohexyl, cyclooctyl, and the like. Examples of multiple ring cycloalkyl groups include, but are not limited to, adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like. The term cycloalkyl group also includes a heterocycloalkyl group, where at least one of the carbon atoms of the ring is substituted with a heteroatom such as, but not limited to, nitrogen, oxygen, sulfur, or phosphorus.

The term "unsubstituted alkyl group" is defined herein as an alkyl group composed of just carbon and hydrogen.

The term "acyl" denotes a group —C(O)R$_{CO}$, in which R$_{CO}$ is hydrogen, optionally substituted alkyl, optionally substituted cycloalkyl, optionally substituted heterocyclyl, optionally substituted aryl, and optionally substituted heteroaryl.

The term "aryl group" as used herein is any carbon-based aromatic group (i.e., aromatic carbocyclic) such as having a single ring (e.g., phenyl) or multiple rings (e.g., biphenyl), or multiple condensed (fused) rings (e.g., naphthyl or anthryl). These may include, but are not limited to, benzene, naphthalene, phenyl, etc.

The term "aryl group" also includes "heteroaryl group," meaning a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen, sulfur, and phosphorus within at least one ring. In other words, heteroaryl groups are aromatic rings composed of at least three carbon atoms that has at least one heteroatom incorporated within the ring of the aromatic group. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO— heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The aryl group can be substituted or unsubstituted. Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, aldehyde, cycloalkyl, cycloalkenyl, acyl, acylamino, acyloxy, amino, aminocarbonyl, alkoxycarbonylamino, azido, cyano, ester, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2. In some embodiments, the term "aryl group" is limited to substituted or unsubstituted aryl and heteroaryl rings having from three to 30 carbon atoms.

The term "aralkyl group" as used herein is an aryl group having an alkyl group or an alkylene group as defined herein covalently attached to the aryl group. An example of an aralkyl group is a benzyl group. "Optionally substituted aralkyl" refers to an optionally substituted aryl group covalently linked to an optionally substituted alkyl group or alkylene group. Such aralkyl groups are exemplified by benzyl, phenylethyl, 3-(4-methoxyphenyl)propyl, and the like.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "alkenyl group" refers to a monoradical of a branched or unbranched unsaturated hydrocarbon group typically having from 2 to 40 carbon atoms, more typically 2 to 10 carbon atoms and even more typically 2 to 6 carbon atoms and having 1-6, typically 1, double bond (vinyl). Typical alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. When alkenyl is attached to nitrogen, the double bond cannot be alpha to the nitrogen.

The term "substituted alkenyl group" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO— heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "cycloalkenyl group" refers to carbocyclic groups of from 3 to 20 carbon atoms having a single cyclic ring or multiple condensed rings with at least one double bond in the ring structure.

The term "alkynyl group" refers to a monoradical of an unsaturated hydrocarbon, typically having from 2 to 40 carbon atoms, more typically 2 to 10 carbon atoms and even more typically 2 to 6 carbon atoms and having at least 1 and typically from 1-6 sites of acetylene (triple bond) unsaturation. Typical alkynyl groups include ethynyl, (—C≡CH), propargyl (or prop-1-yn-3-yl, —CH$_2$C≡CH), and the like. When alkynyl is attached to nitrogen, the triple bond cannot be alpha to the nitrogen.

The term "substituted alkynyl group" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "alkylene group" is defined as a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene group" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), and the like.

The term "alkoxy group" refers to the group R—O—, where R is an optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio group" refers to the group R$_S$—S—, where R$_S$ is as defined for alkoxy.

The term "aminocarbonyl" refers to the group —C(O)NR$_N$R$_N$ where each R$_N$ is independently hydrogen, alkyl, aryl, heteroaryl, heterocyclyl or where both R$_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "acylamino" refers to the group —NR$_{NCO}$C(O)R where each R$_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "aryloxy group" refers to the group aryl-O— wherein the aryl group is as defined above, and includes optionally substituted aryl groups as also defined above.

The term "heteroaryloxy" refers to the group heteroaryl-O—.

The term "amino" refers to the group —NH$_2$.

The term "substituted amino" refers to the group —NR$_w$R$_w$ where each R$_w$ is independently selected from the group consisting of hydrogen, alkyl, cycloalkyl, carboxyalkyl (for example, benzyloxycarbonyl), aryl, heteroaryl and heterocyclyl provided that both R$_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "carboxy" refers to a group —C(O)OH. The term "carboxyalkyl group" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, and —S(O)$_n$R$_{SO}$, in which R$_{SO}$ is alkyl, aryl, or heteroaryl and n is 0, 1 or 2.

The term 'cinnamate' refers to a salt or ester of cinnamic acid, which is an organic compound with the formulate C$_6$H$_5$CH=CHCOOH. Both cinnamic acids and cinnamates are classified as unsaturated carboxylic acids. Cinnamates may occur as both cis and trans isomers.

The term 'chalcone' refers to an aromatic ketone and an enone that forms the central core for a variety of important biological compounds, collectively as chalcones or chalconoids. Examples of chalcones include benzylideneacetophenone, phenyl styryl ketone, benzalacetophenone, β-phenylacrylophenone, γ-oxo-α,γ-diphenyl-α-propylene, and α-phenyl-β-benzoylethylene.

The term 'coumarin' (i.e., 2H-chromen-2-one) refers to an aromatic organic chemical compound with formula C$_9$H$_6$O$_2$. It is a benzene molecule with two adjacent hydrogen atoms replaced by a lactone-like chain —O—, forming a second six-membered heterocycle that shares two carbons with the benzene ring. It may be placed in the benzopyrone chemical class and considered as a lactone.

The terms "substituted cycloalkyl group" or "substituted cycloalkenyl group" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO— heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect. In some embodiments, "conjugated groups" is limited to conjugated groups having three to 30 carbon atoms.

The term "halogen," "halo," or "halide" may be referred to interchangeably and refer to fluoro, bromo, chloro, and iodo.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO— alkyl, —SO-aryl, —SO— heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "thiol" refers to the group —SH. The term "substituted alkylthio" refers to the group —S— substituted alkyl. The term "arylthiol group" refers to the group aryl-S—, where aryl is as defined as above. The term "heteroarylthiol" refers to the group —S— heteroaryl wherein the heteroaryl group is as defined above including optionally substituted heteroaryl groups as also defined above.

The term "sulfoxide" refers to a group —S(O)R$_{SO}$, in which R$_{SO}$ is alkyl, aryl, or heteroaryl. The term "substituted sulfoxide" refers to a group —S(O)R$_{SO}$, in which R$_{SO}$ is substituted alkyl, substituted aryl, or substituted heteroaryl, as defined herein. The term "sulfone" refers to a group —S(O)$_2$R$_{SO}$, in which R$_{SO}$ is alkyl, aryl, or heteroaryl. The term "substituted sulfone" refers to a group —S(O)$_2$R$_{SO}$, in which R$_{SO}$ is substituted alkyl, substituted aryl, or substituted heteroaryl, as defined herein.

The term "keto" refers to a group —C(O)—. The term "thiocarbonyl" refers to a group —C(S)—.

As used herein, the term "room temperature" is 20° C. to 25° C.

Disclosed are compounds, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B—F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B—F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A weight percent of a component, unless specifically stated to the contrary, is based on the total weight of the formulation or composition in which the component is included.

Detection of health conditions by non-invasive ways is one major goal of current medical research. In such an approach, it is critical to connect the physiological condition inside the human body to a detectable metric measured outside the human body. In other words, non-invasive methods involve measuring some benchmark external to the body that provides cues as to a physiological condition inside the body. In one application, gases emitted from humans may be linked to certain diseases. For example, content of ammonia in the breath may be an indicator for kidney diseases, acetone an indicator for diabetes, and nitric oxide an indicator for asthma. Gas emission may also be detected through the skin.

Disclosed herein are highly-sensitive vertical gas sensors for detection of gas emitted from skin of humans. The gas sensor has a vertical channel with organic semiconductors, and in some examples, has a sensitivity of ammonia detection to as low as 30 parts-per-billion (ppb) using the electrical current responses. The gas sensor is also sensitive to aldehyde (e.g., comprising 7-9 carbon atoms) detection. Gas samples may be collected from various skin positions such as the hand (e.g., palm), forehead, forearm, chin, and elbow.

Devices

An organic vertical transistor is similar to a solid-state version of a vacuum tube triode. The vacuum tube triode consists of the cathode for electron emission by heating, the anode for electron collection, and the grid for current modulation. The anode is always positively biased against the cathode. In a vacuum tube triode, both the grid and anode electrodes can control the potential within the device, but the grid is much more effective in controlling the gradient near the cathode. The on and off state of the vacuum tube triode is determined by whether the emitted electrons encounter a large energy barrier between cathode and anode or not. When the grid is in large and negative bias, the electrons experience a negative gradient of potential after they are emitted from cathode, and consequently very few of them can be collected by the anode. However, if the grid is slightly negative biased or positively biased, it is possible for the electrons to find a passage through the potential minimum in the grid.

One example of an organic vertical transistor design that function similar to the vacuum tube triodes is shown in FIG. 1. The device is on an inert substrate, such as glass or polymer. Ultrathin (less than 150 or 100 µm for example) and flexible glasses allow the device to be placed in a variety of locations. Electrons are injected from the emitter, going through the openings on the metal grid and finally arriving at the collector. The collector can be a metals, alloys, or metal oxide capable of properly operating at the voltages and currents of the device. Example materials that can be used include Al, Au, Ag, Pt, Cu, and stainless steel. The emitter can have a thickness of 10 nm or greater, for example 10 nm to 500 nm, with the thickness being dictated by the material, signal, current and voltage.

The metal grid can similarly be made of metals capable of properly operating at the voltages and currents of the device, such as Al, Au, Ag, Pt, Cu, and stainless steel. In some embodiments, the metal grid and collector are made of the same material. The metal grid can have a thickness of 10 nm or greater, for example from 10 nm to 200 nm, with the thickness being dictated by the material, the size of the passages through the grid, current and voltage.

The emitter may be a metal, metal oxide, or polymer with a thickness from 10 nm to 500 nm, again dictated by the material, signal, current and voltage. Example materials for the emitter poly(3,4-ethylenedioxythiophene):poly(styrenesulfonate) (PEDOT:PSS), transparent conductive oxides such as indium tin oxide (ITO), and metals such as Cu, Pt, Au, Ag, and the like.

The potential between emitter and collector can be controlled by the voltages of the grid and collector. When voltages of the grid and collector constitute a high barrier between the emitter and the opening, few carriers can arrive at the collector through the openings. On the other hand, if there is no barrier the carriers can go through the opening and reach the collector. The magnitude of the collector current is determined by the space-charge-limited current given by the potential difference between the emitter and the center of the opening. Collector current is modulated by the grid bias which controls the effective potential at the opening for fixed emitter and collector potentials.

For vertical transistors, the output current density is proportional to the vertical mobility according to the space-charge-limited current relation:

$$J_{SCLC}=(9/8)\varepsilon_0\varepsilon_r\mu(V^2/L^3).$$

where, J is current density, $\varepsilon_0$ is permittivity in vacuum space ($8.854\times10^{-12}$ F/m), $\varepsilon_r$ is relative permittivity, $\mu$ is charge carrier mobility, V is voltage between electrodes, and L is material of thickness.

The advantages of using a donor-acceptor organic semiconductor material in such a system are that the material generates a high current density and high mobility and is highly stable (long shelf life), allowing for simplification of the devices because they can be made without need of an encapsulating layer. Further, many of the polymers can be made efficiently in using non-toxic processes at high purities and high molecular weights (up to 120,000 Da), and with solvent-based printing processes that produce a uniformly thin semiconducting layer.

Use of high performance donor-acceptor type of organic semiconductors provide distinct advantages when combined with this unique vertical transistor structure. For example, operation voltages for the vertical transistor may be 2V or less, 1.5V or less, 1.25V or less or 1V or less. The donor-acceptor based vertical transistor may have current densities of at least 80 mA/cm$^2$, 90 mA/cm$^2$, 100 mA/cm$^2$, 110 mA/cm$^2$, 120 mA/cm$^2$, 130 mA/cm$^2$, 140 mA/cm$^2$, 150 mA/cm$^2$, or 160 mA/cm$^2$. Because there is no need for an encapsulation layer, the device fabrication process is simpler and scalable for large area requiring a little as two mask levels and allowing for the use of a variety of hydrocarbon solvents.

Device fabrication to produce the device in FIG. 1 is conducted as follows: A layer of polyvinylpyrrolidone (PVP) is spin coated on the ITO emitter from 8 wt. % PVP:PGMEA solution to serve as an insulating layer. A thin surface modification layer (e.g., poly(3-hexylthiophene-2,5-diyl); P3HT) is coated on PVP to modify the surface energy. Then, polystyrene (PS) spheres (diameter: 200 nm) are adsorbed on the substrate. To prepare a layer of self-assembled PS spheres on a PVP substrate, the substrate is dipped inside the ethanol solution of spheres (1.4 wt. %) for 90 sec. The spheres are adsorbed on the substrate surface and the wet substrate is then taken out of the ethanol and dipped into boiling isopropyl alcohol (IPA) to rinse away the spheres that are not adsorbed. A stream of nitrogen gas is used to blow-dry the hot IPA to form a monolayer of spheres. The PS spheres serve as a hard mask for the following deposition of the metal grid layer (Al). A layer of Al (40 nm) and a layer of SiO (50 nm) were deposited as an electrode and an insulating layer, respectively. After removing the spheres by Scotch type (3M), openings in the metal grid are formed. Oxygen plasma is used to etch through the PVP to open a channel and to form aluminum oxide on top of the grid. The device is then finished by the deposition of an embodied donor-acceptor organic semiconductor layer (~200-600 nm thick) and then patterning of collector (MoO$_3$/Al).

In particular, the vertical transistor provides a unique design that allows for high amplification and improves sensitivity of organic semiconductors in senor applications. In the vertical transistor design, device current is through the bulk material and is not hampered by surface effects like normal field mobility degradation or proximity doping effects as in FETs. Further, the vertical design encapsulates the OSC, thus enhancing the stability of the device and OSC material. Finally, the vertical OSC transistor occupies a much smaller in footprint than a traditional device such as a FET. A planar FET would need to be ~150× to 200× the footprint size to achieve the same current output.

Organic Semiconductor (OSC) Compounds

Presented herein are conjugated polymeric and small molecule compounds that may be used in vertical transistors, and electronic devices incorporating such transistors. The compounds may be easily synthesized and may be solution processable. Accordingly, transistors incorporating these compounds may be manufactured using solution deposition techniques such as inkjet printing, dip and/or spin coating, and screen printing, to name a few.

OSC Polymers

Polymeric compounds described herein contain alternating blocks of aromatic, heteroaromatic or ethynylene electron accepting groups ("A" groups, also referred to as electron withdrawing groups or electron accepting groups), which are referred to as acceptor blocks, and blocks of aromatic or heteroaromatic electron-rich donating groups ("D" groups, also referred to as electron donating groups), which are referred to as donor blocks, along a compound backbone. The acceptor blocks contribute to the electron transport, while the donor blocks contribute to the hole transport.

The repeating unit of the polymeric compounds contains an acceptor block containing one or more acceptor groups (A) with a donor block containing one or more donor groups (D) on each side of the acceptor group, thus providing the general Formula I:

(I)

where a and b are integers from 1 to 4 and n is an integer from 2 to 10,000, each D is an independently selected conjugated electron donating aromatic or heteroaromatic group having from 5 to 50 backbone atoms, each D group optionally substituted with one or more electron donating substituents or electron withdrawing substituents, provided that even when substituted the electronic character of each D is electron donating; each A is an independently selected conjugated electron accepting aromatic or heteroaromatic group having from 5 to 50 backbone atoms or an ethynylene group substituted with one or two electron withdrawing substituents, each A being optionally substituted with one or more electron donating substituents or electron withdrawing substituents provided that even when substituted the electronic character of each A is electron accepting.

Examples of organic compounds having the structures of Formula I are as follows. In some examples, each D is independently one or more of the following in Table 1:

TABLE 1

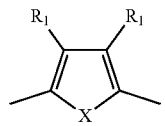

TABLE 1-continued
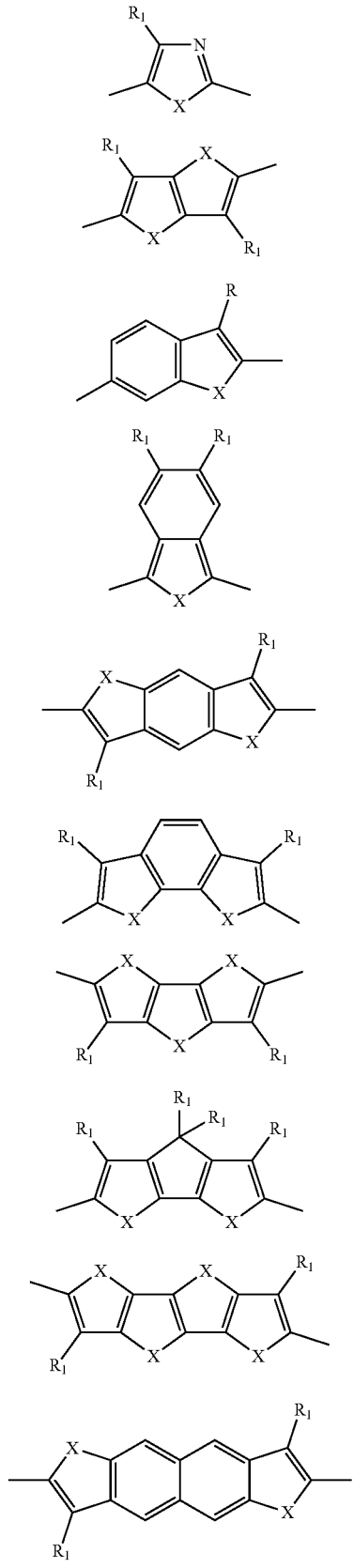
TABLE 1-continued
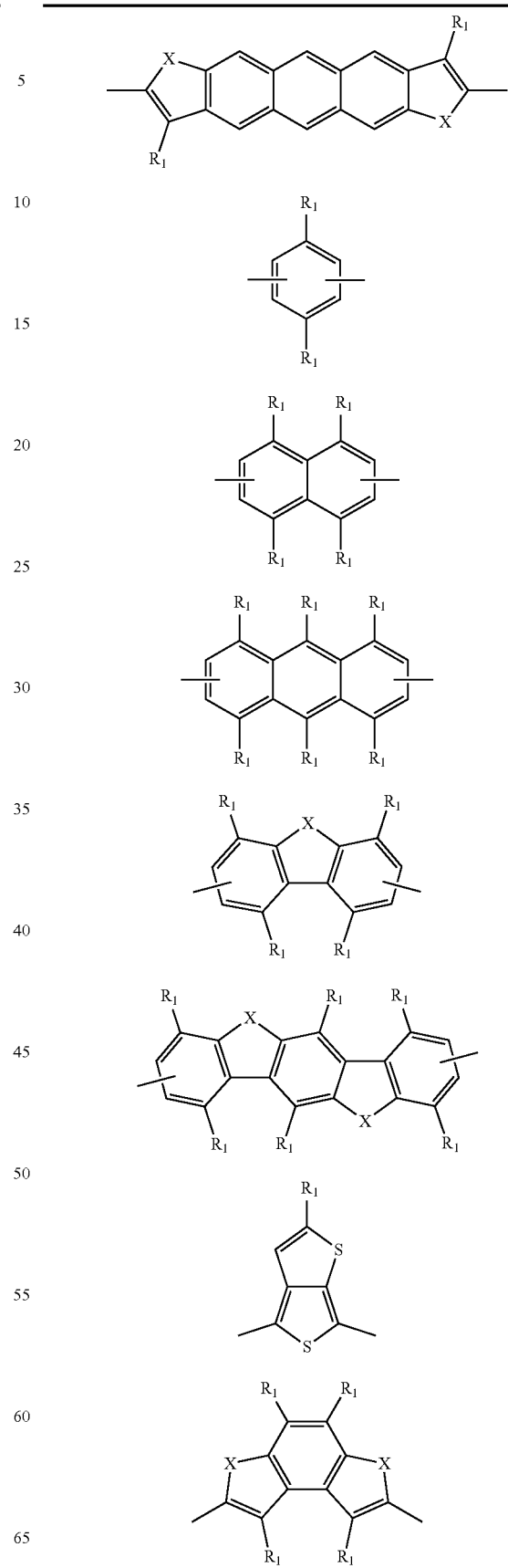

TABLE 1-continued

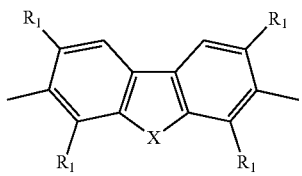

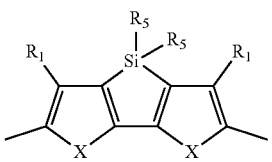

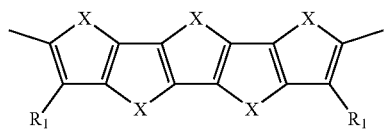

where each x is independently NR$_6$, S, Se, or O; each R$_1$ is independently hydrogen, C$_1$-C$_{40}$ alkyl, C$_1$-C$_{40}$ alkenyl, alkynl, alkoxy, cycloalkyl, C$_1$-C$_{40}$ aryl, C$_1$-C$_{40}$ heteroaryl, C$_1$-C$_{40}$ heterocycloalkyl, C$_1$-C$_{40}$ conjugated group, any of which may be optionally substituted, or halo; each R$_5$ is independently hydrogen, C$_1$-C$_{40}$ alkyl, C$_1$-C$_{40}$ alkenyl, C$_1$-C$_{40}$ alkoxy, C$_1$-C$_{40}$ cycloalkyl, C$_1$-C$_{40}$ aryl, C$_1$-C$_{40}$ heteroaryl, or C$_1$-C$_{40}$ conjugated group, any of which may be optionally substituted; and each R$_6$ is independently hydrogen, C$_1$-C$_{40}$ alkyl.

In some examples, each A is independently one or more of the following in Table 2:

TABLE 2

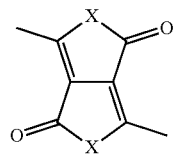

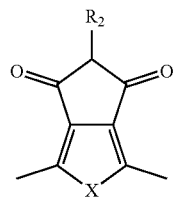

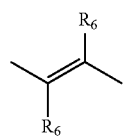

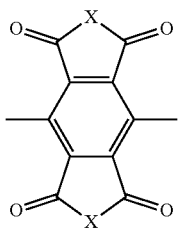

TABLE 2-continued

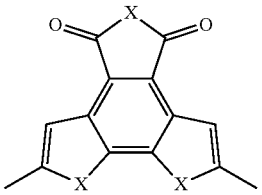

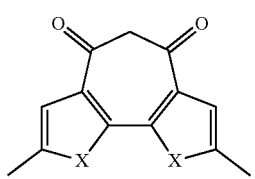

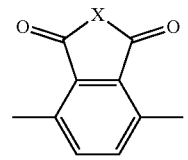

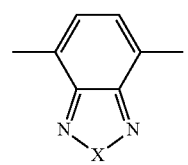

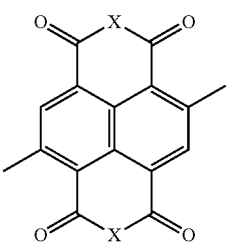

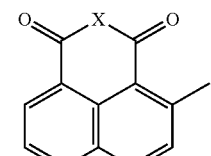

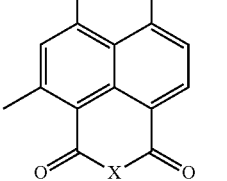

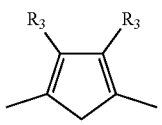

TABLE 2-continued

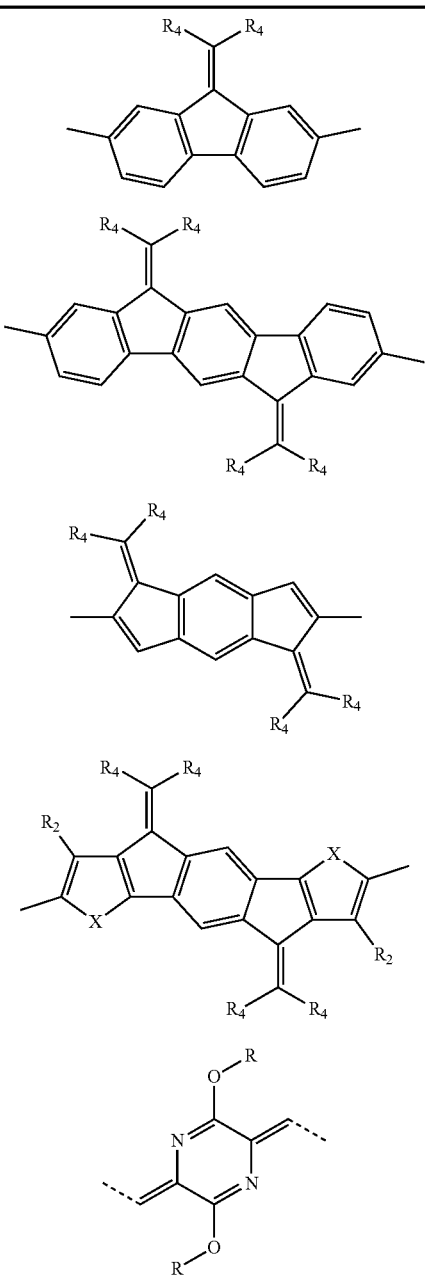

where each x is independently $NR_5$, S, Se, or O; each $R_2$ is independently hydrogen, $C_1$-$C_{40}$ alkyl, $C_1$-$C_{40}$ alkenyl, $C_1$-$C_{40}$ alkynl, $C_1$-$C_{40}$ alkoxy, $C_1$-$C_{40}$ cycloalkyl, $C_1$-$C_{40}$ aryl, $C_1$-$C_{40}$ heteroaryl, $C_1$-$C_{40}$ heterocycloalkyl, $C_1$-$C_{40}$ conjugated group, any of which may be optionally substituted, or halo; each $R_3$ is independently hydrogen, $C_1$-$C_{40}$ alkyl, $C_1$-$C_{40}$ alkenyl, $C_1$-$C_{40}$ alkoxy, $C_1$-$C_{40}$ cycloalkyl, $C_1$-$C_{40}$ aryl, $C_1$-$C_{40}$ heteroaryl, or $C_1$-$C_{40}$ conjugated group, any of which may be optionally substituted; each $R_5$ is independently hydrogen, $C_1$-$C_{40}$ alkyl; each $R_4$ is independently hydrogen, $C_1$-$C_{40}$ alkyl, cyano, ester, or carboxylic acid, and each $R_6$ is independently hydrogen, $C_1$-$C_{40}$ alkyl, cyano, ester, or carboxylic acid.

The side chains, $R_1$, $R_2$, $R_3$, $R_4$, and $R_6$ can play a significant role in the solubility, stability, or film forming properties (including structure, adhesion, organization, processability, and the like) of the polymers. In some examples, one or more of $R_1$, $R_2$, $R_3$, $R_4$, and $R_6$ is an optionally substituted $C_{15}$-$C_{35}$ alkyl. In some examples, one or more of $R_1$, $R_2$, $R_3$, or $R_4$ is an optionally substituted $C_{15}$-$C_{35}$ alkyl having at least one branching point. In particular, one or more of $R_1$, $R_2$, or $R_3$ can be optionally substituted $C_{15}$-$C_{35}$ alkyl. In some examples, each $R_1$ or $R_2$ is independently an optionally substituted $C_{15}$-$C_{35}$ alkyl. In some examples, each $R_1$ or $R_2$ is independently an optionally substituted $C_{15}$-$C_{35}$ alkyl having at least one branching point. In some examples, each $R_1$ or $R_2$ is independently an optionally substituted $C_{15}$-$C_{35}$ alkyl having at least one branching point, where the branching point is at least 4 carbons from the base molecule.

While it may be expected that the large, branched alkyl side chains would inhibit stacking or structured organization of the polymer, these potential issues have not been observed. While not wanting to be bound by theory, it is hypothesized that the embodied polymers provide superior properties when branched alkyl chains are at least four carbons away from the main polymer backbone, thereby producing no or very low steric effect, which would interfere with the π-stacking of the polymer backbones, and the existence of four large, nonpolar branched side chains in one polymer repeat unit significantly increases the solubility of these polymers, thus allowing for an increase in the molecular weight of the polymers, which may result in an enhanced mobility over current high performance polymers. In some examples, the polymers have molecular weights of from about 30-80 kDa or 40-60 kDa.

In some examples, organic compounds having the structure of Formula I may be exemplified in Table 3, wherein n is an integer from 2 to 10,000:

TABLE 3

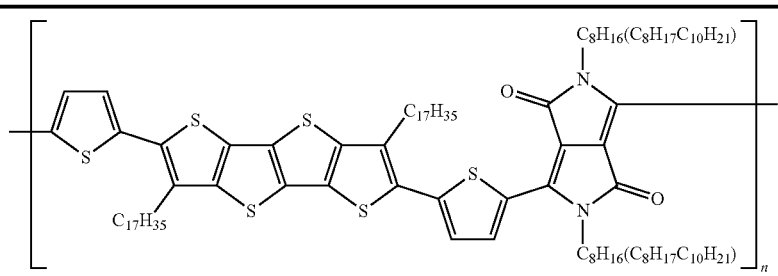

TABLE 3-continued
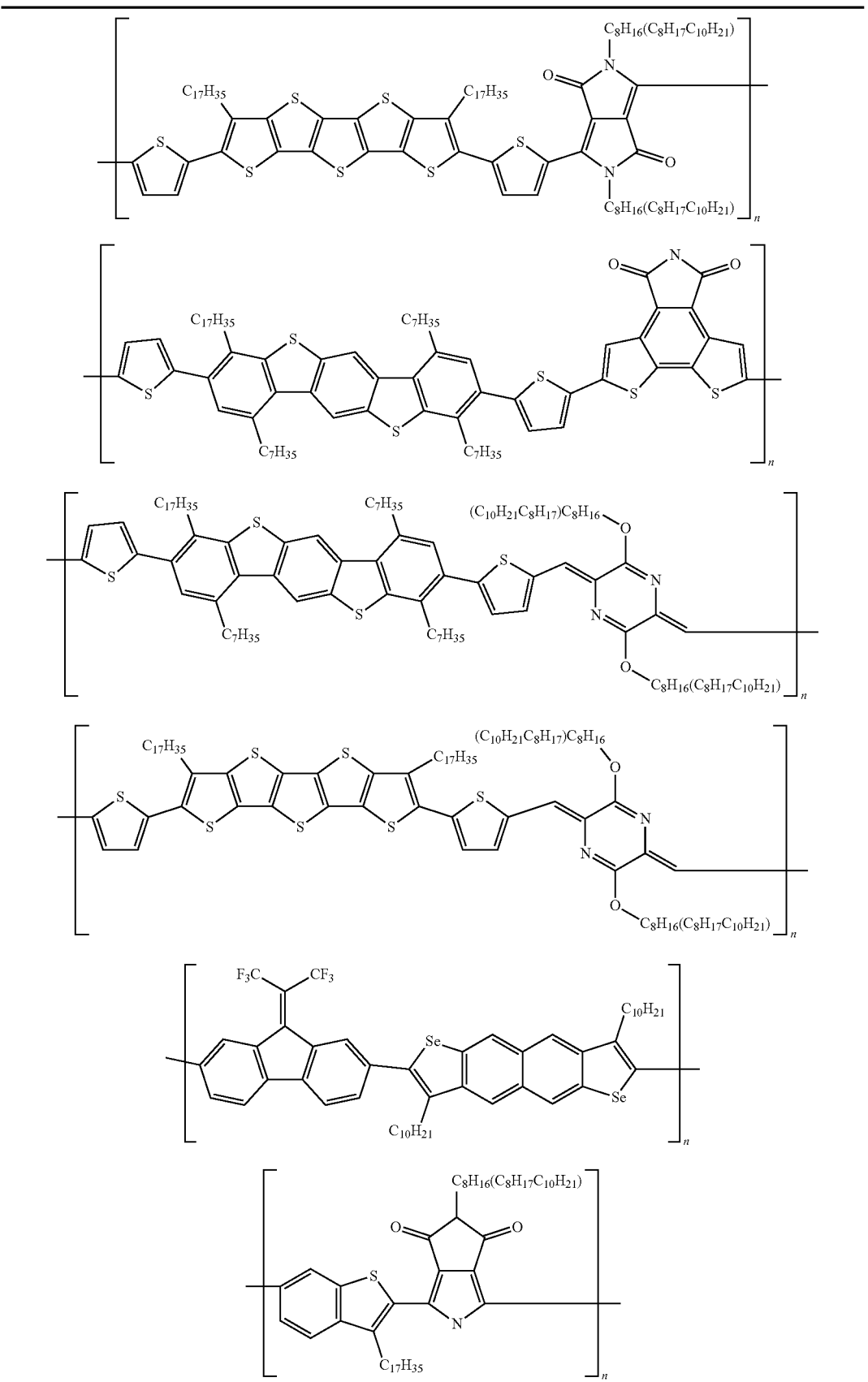

TABLE 3-continued
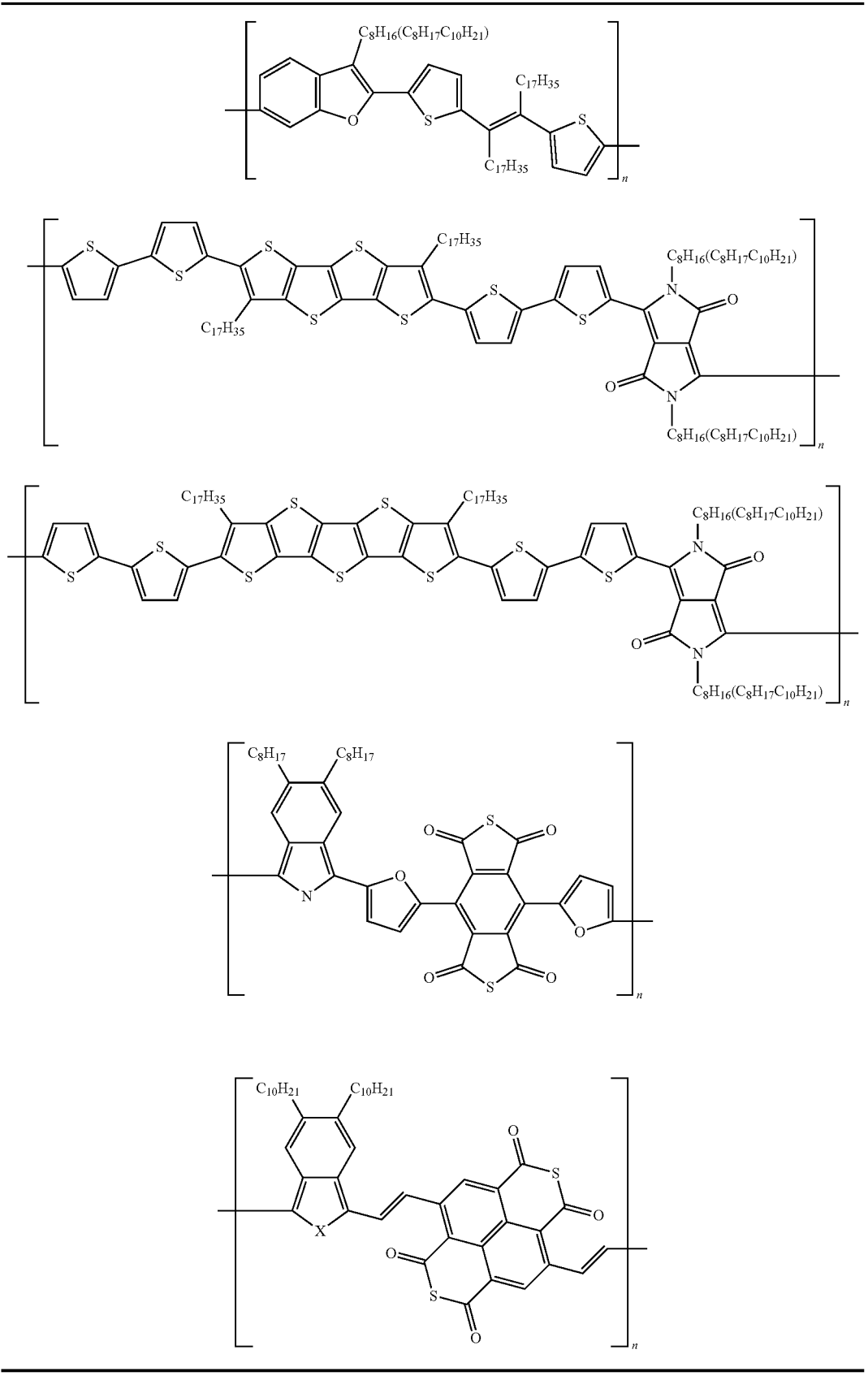

In some examples, the OSC polymers may be n-type, p-type and ambipolar polymers, as exemplified in Table 4 below, wherein n is an integer from 2 to 10,000:
TABLE 4
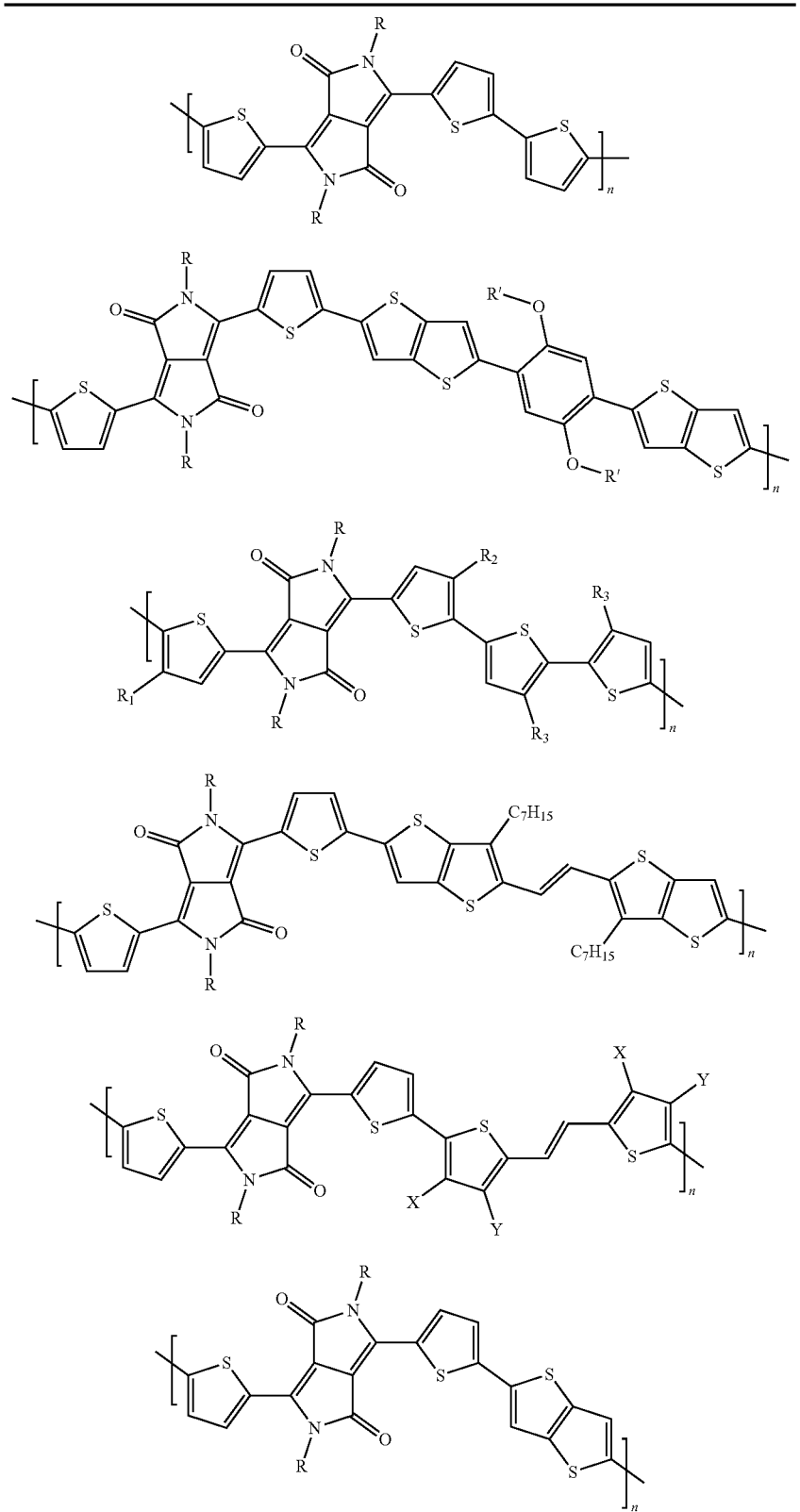

TABLE 4-continued
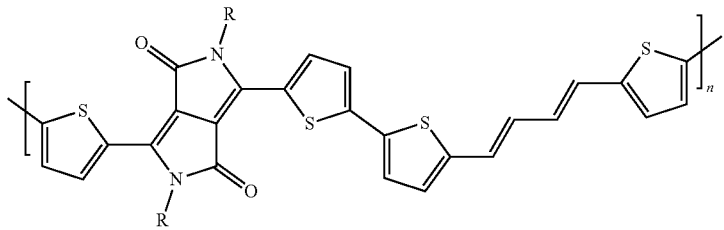
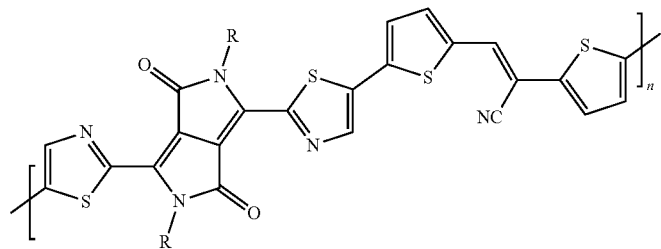
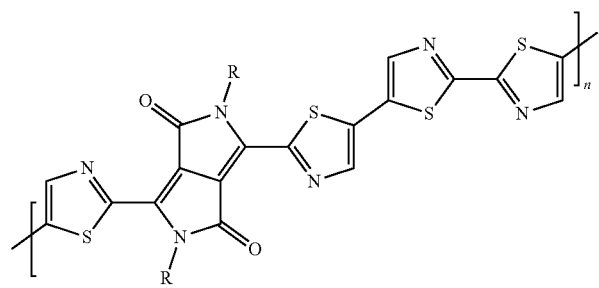
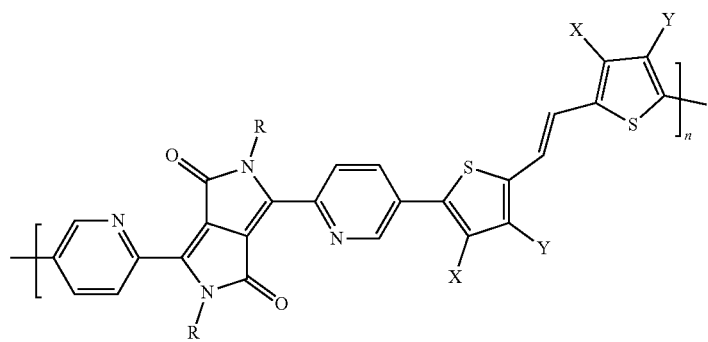
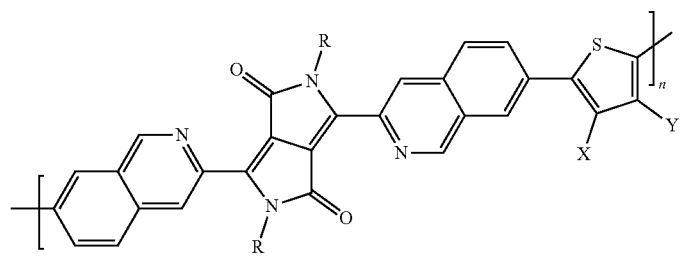
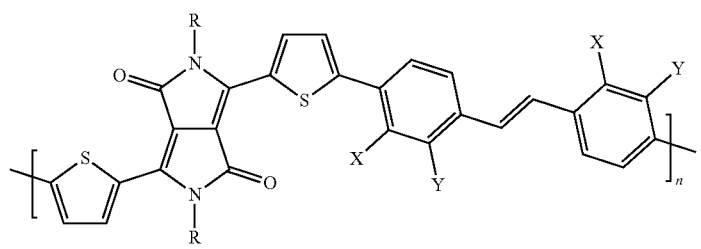

TABLE 4-continued
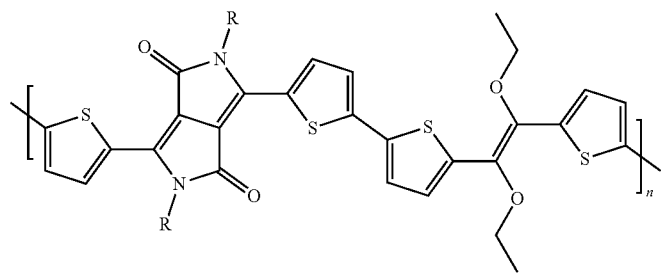
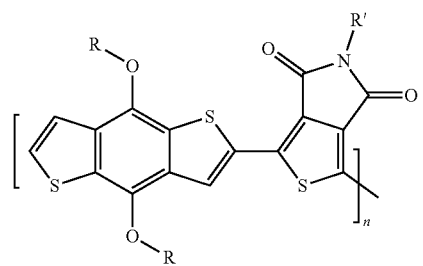
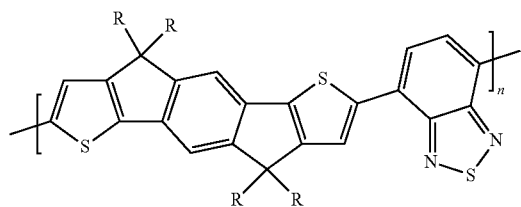
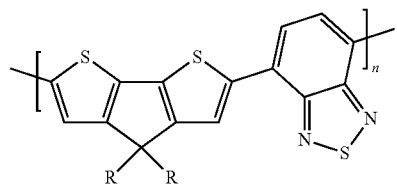
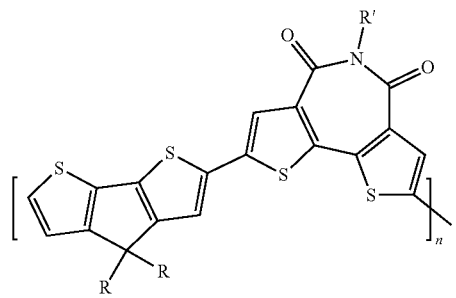
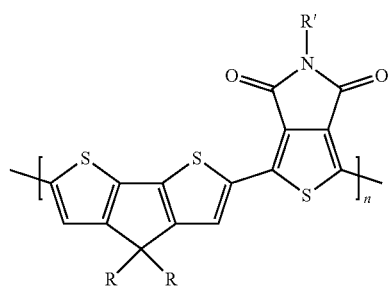

TABLE 4-continued
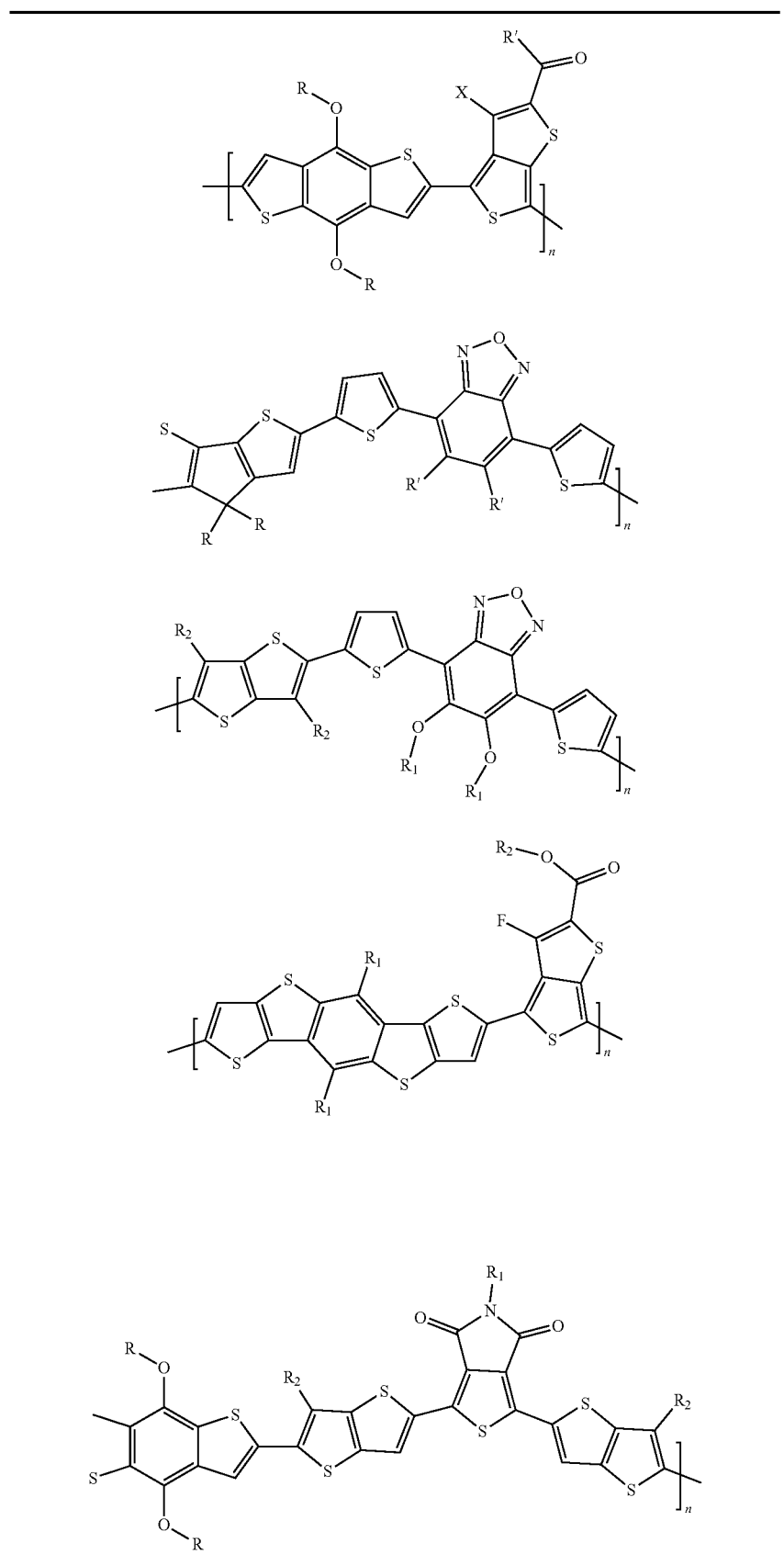

TABLE 4-continued
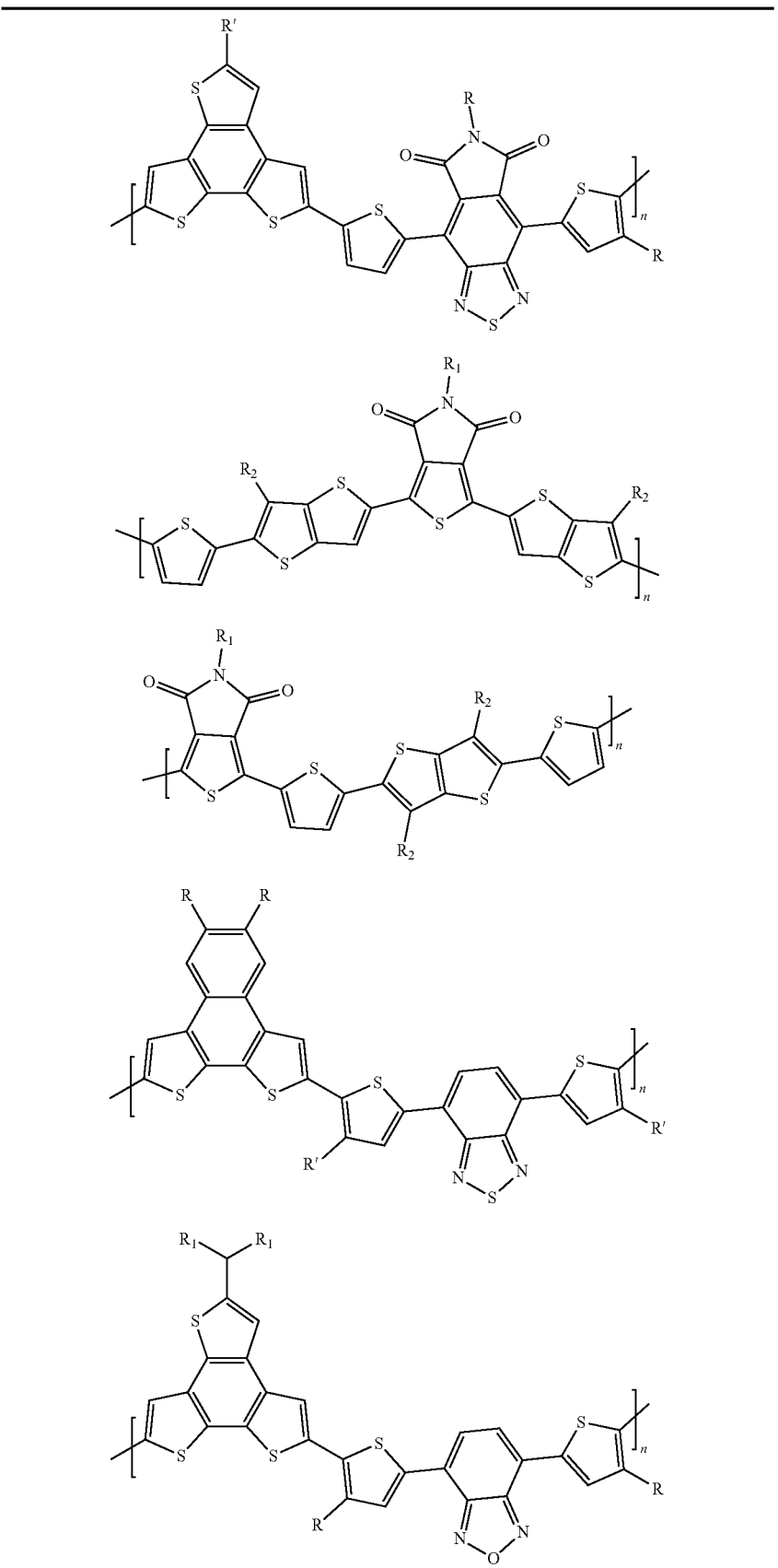

TABLE 4-continued
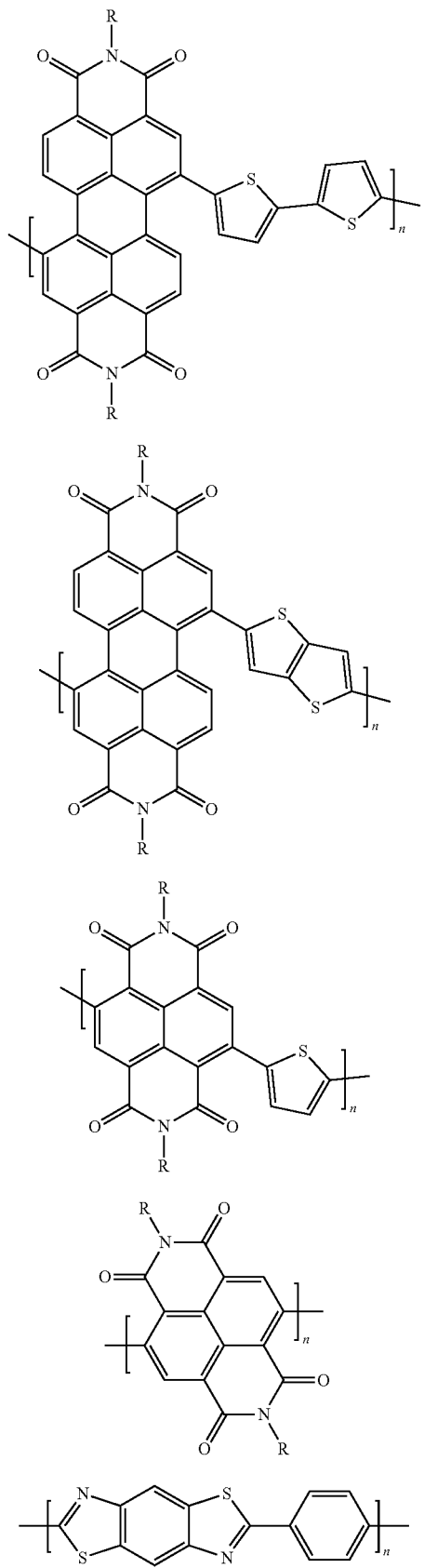

TABLE 4-continued
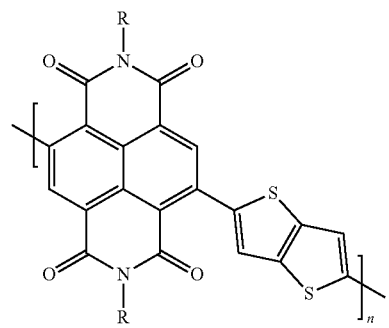
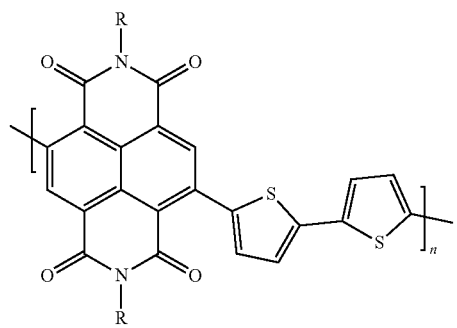
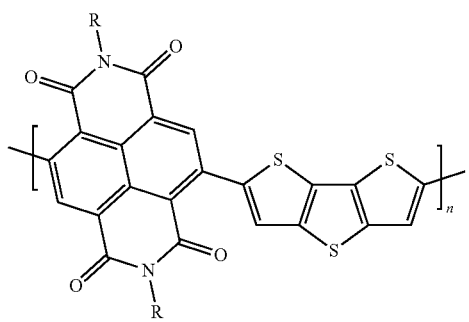
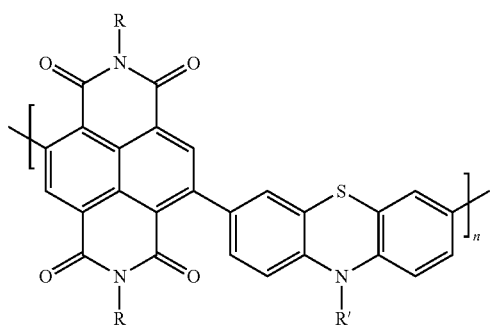
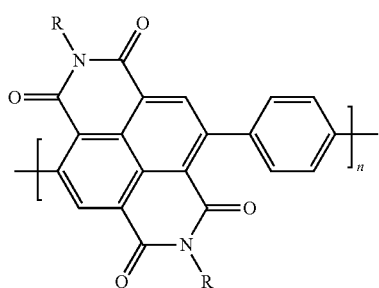

TABLE 4-continued
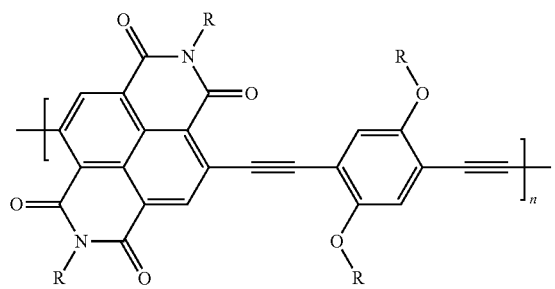
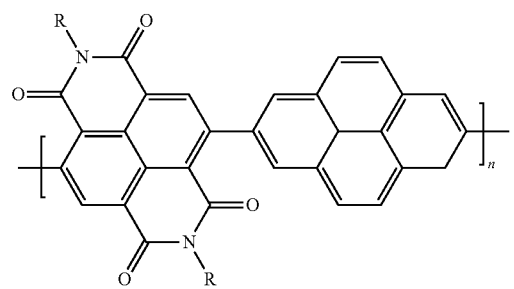
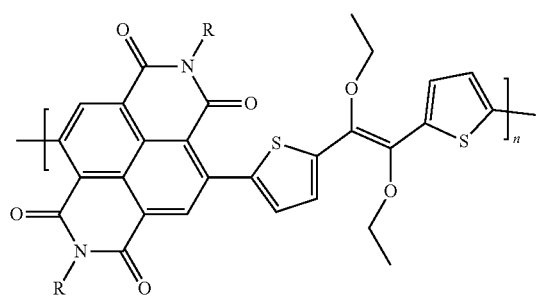
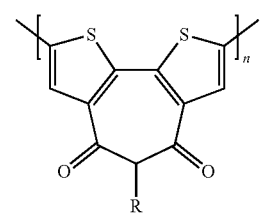
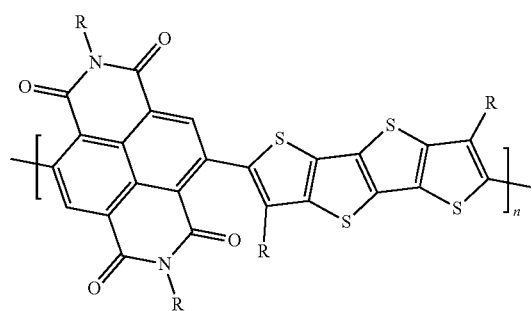

TABLE 4-continued
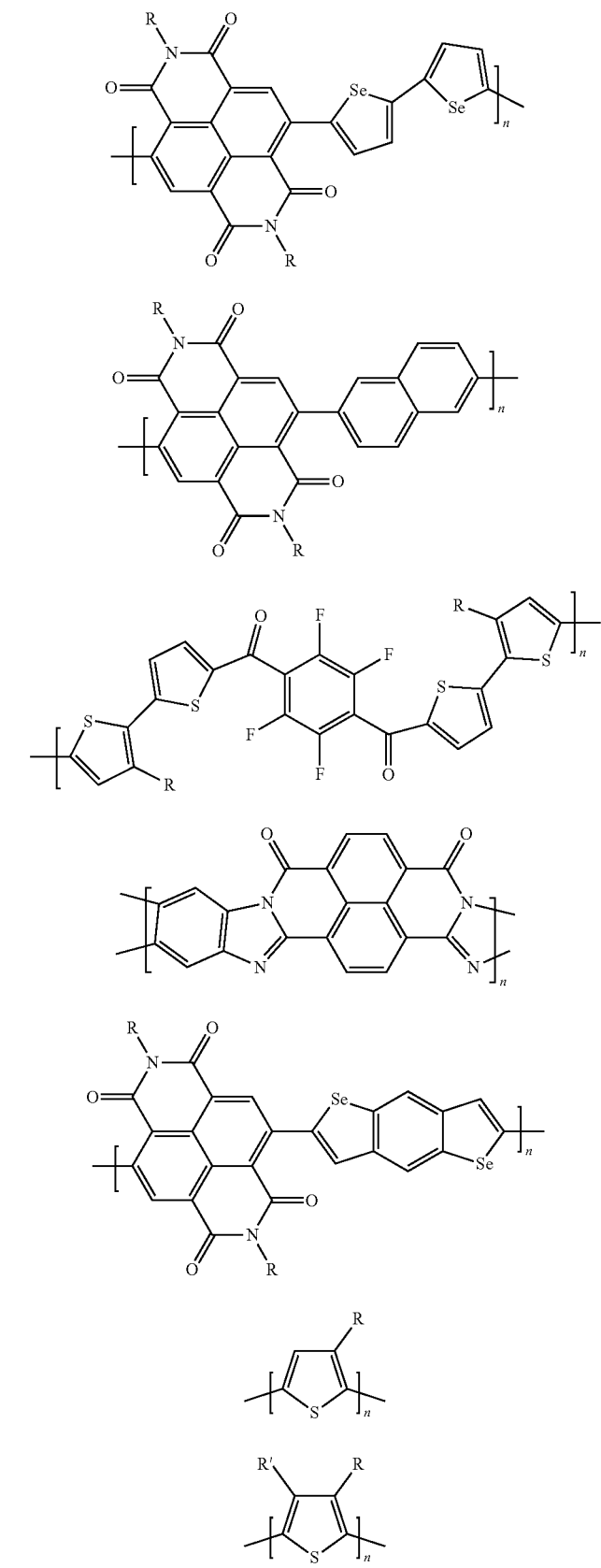

TABLE 4-continued

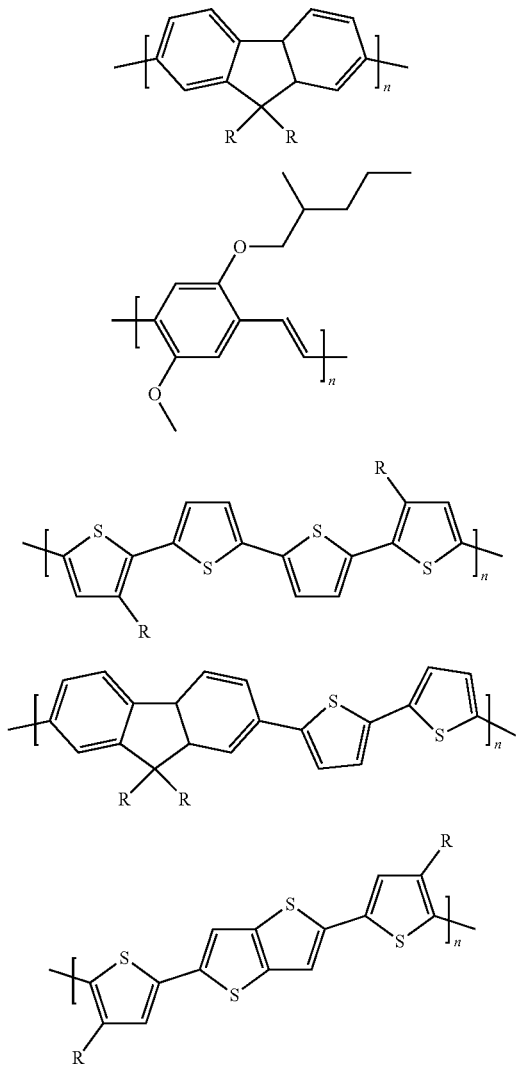

In Table 4, R, R', $R_1$, $R_2$, X, and Y are each independently selected as hydrogen, $C_1$-$C_{40}$ alkyl, $C_1$-$C_{40}$ alkenyl, $C_1$-$C_{40}$ alkynl, $C_1$-$C_{40}$ alkoxy, $C_1$-$C_{40}$ cycloalkyl, $C_1$-$C_{40}$ aryl, $C_1$-$C_{40}$ heteroaryl, $C_1$-$C_{40}$ heterocycloalkyl, $C_1$-$C_{40}$ conjugated group, any of which may be optionally substituted, or halo.

OSC Small Molecules

In some examples, soluble OSC small molecules may be used either solely or in combination with OSC polymers, such as those defined in Tables 1-4. In some examples, small organic compounds are exemplified in Table 5:

TABLE 5

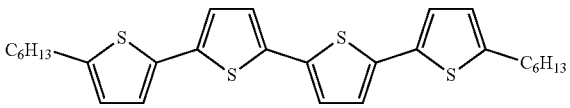

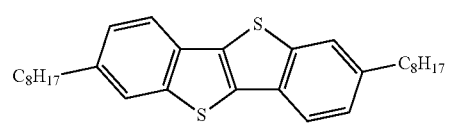

TABLE 5-continued
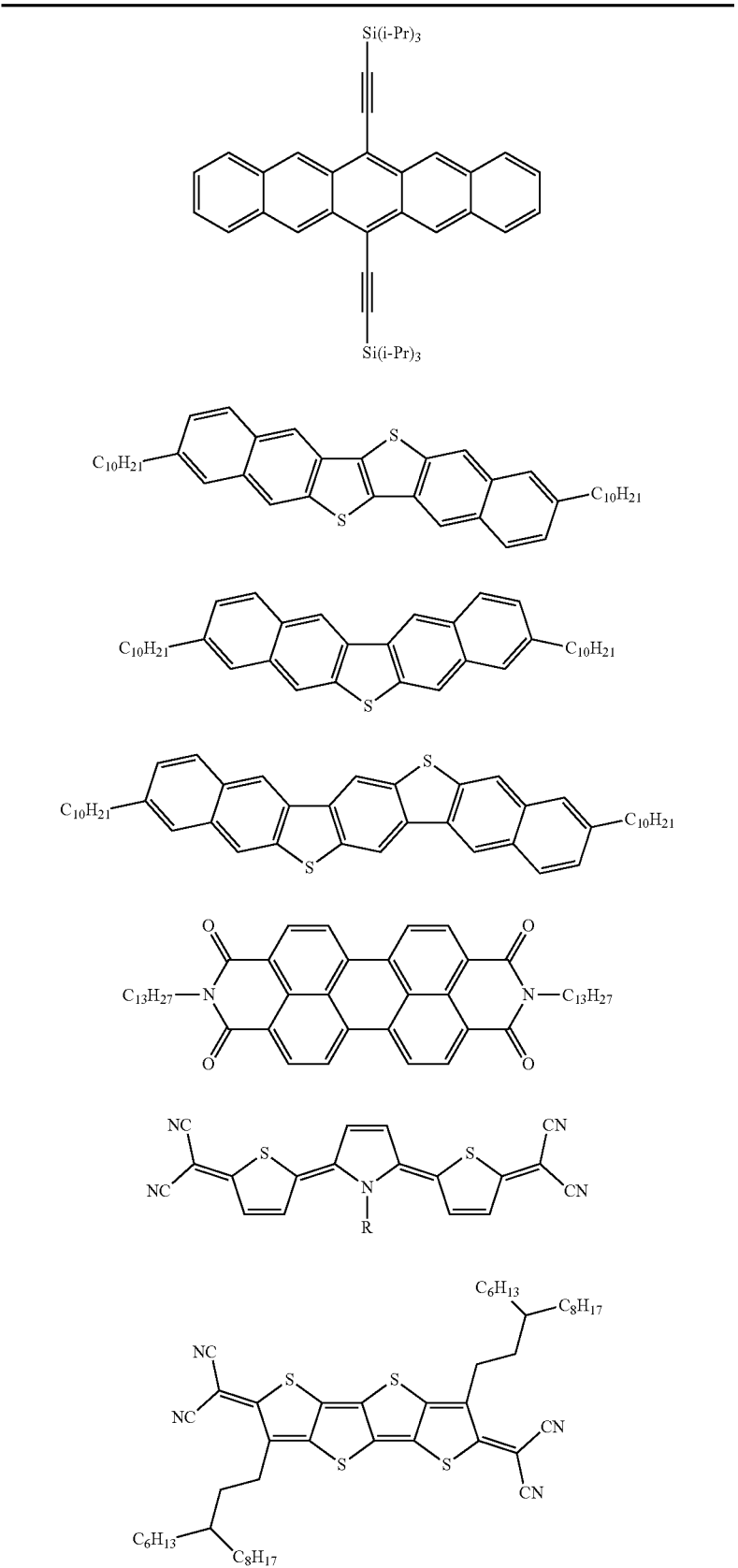

TABLE 5-continued
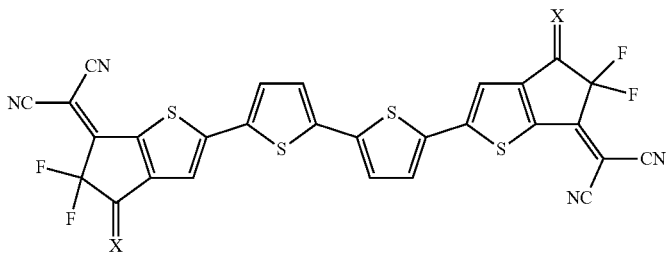
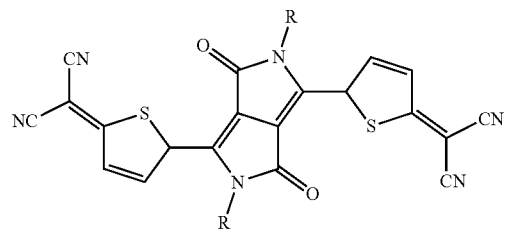
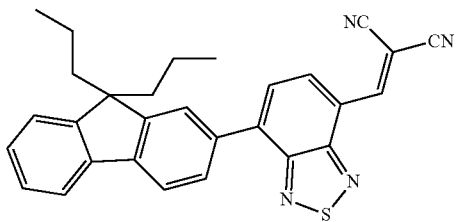 [SMILES: CCCC1(CCC)c2ccccc2-c2ccc(-c3ccc(C=C(C#N)C#N)c4nsnc34)cc21]
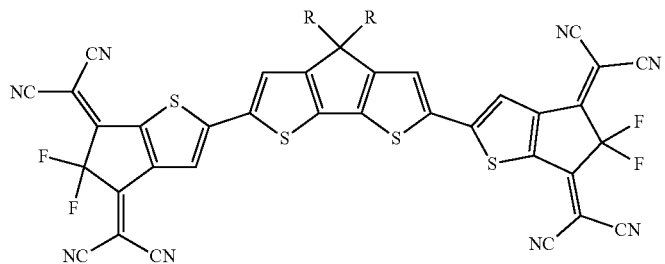
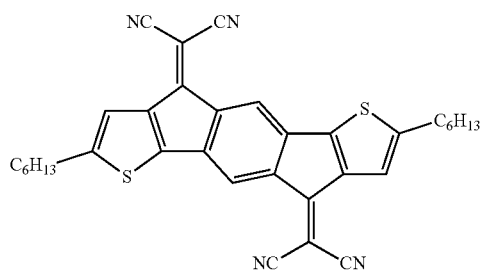
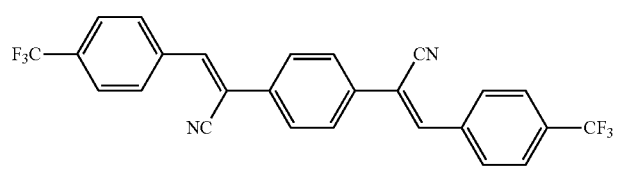 [SMILES: N#C/C(=C\c1ccc(C(F)(F)F)cc1)c1ccc(/C(C#N)=C/c2ccc(C(F)(F)F)cc2)cc1]

TABLE 5-continued

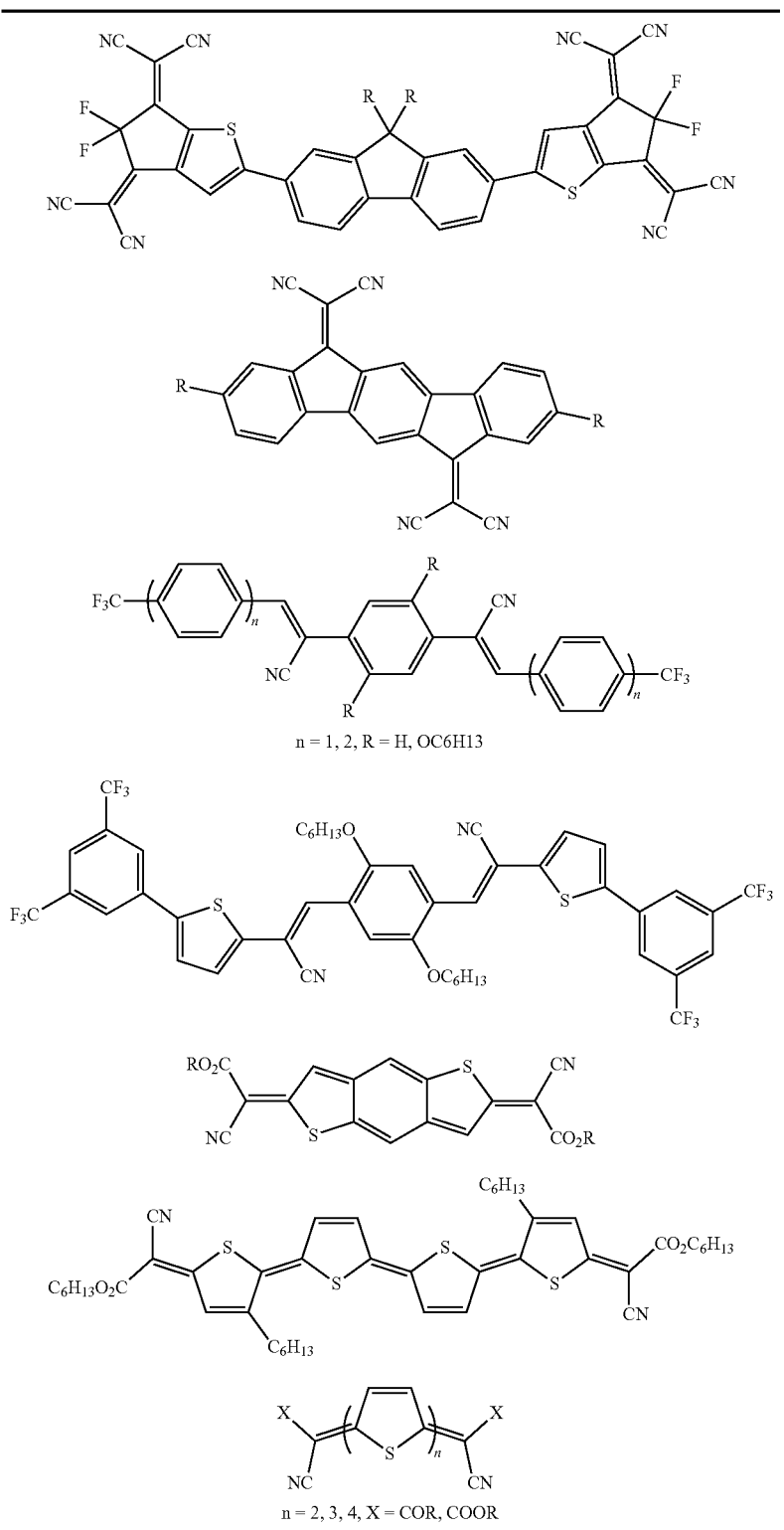

Methods

Another aspect comprises methods of making the compounds and devices described herein. Synthesis of the disclosed monomers, oligomers and polymers can be done without undue experimentation based on references in the literature. Example embodied compounds may be found, for example, in U.S. Pat. Nos. 7,705,108, 7,838,623, 8,389,669, 7,893,191, and 8,624,232, all of which are incorporated herein by reference in their entirety.

Construction of embodied devices is conducted by using an inert, non-conductive substrates that can be subjected to the necessary conditions to produce the device, including elevated temperatures and organic solvents. Glass, glass ceramics, ceramics, and some plastics may be used. The substrate thickness is based on the needs of the device, such as stability or strength. In some examples, the substrate is a glass. In some examples, the substrate is an ultrathin and/or flexible glass, such as Corning® Willow® glass. Generally, it may be preferable to have the substrate be transparent where the device is going to be used in a display or emission-based application. A conductive or emitter layer is then placed on the substrate. For example, a transparent conductive oxide can be coated onto the substrate via known methods such as sputter coating. Alternatively, the emitter may comprise a transparent conductive oxide that is sputter coated on the substrate in combination with a polymer layer is then spin coated on the TCO.

In some examples, an insulating layer can be coated on the emitter layer. The insulating layer can be a polymer layer, such as polyvinylpyrrolidone (PVP) that incorporates polymer spheres (for example, made of polystyrene and having a diameter of from 30-400 nm) that can be later removed. The insulating layer is then coated with a metal mask layer is produced using one or more known methods, including lithography. The polymer spheres are then removed via solvent, leaving voids in the insulating layer and mask. The device is then coated with an OSC compound (s) described herein and finally a collector layer is lithographically patterned on the OSC layer.

In devices with no insulating layer, a first layer of the OSC compound(s) can be coated on the emitter. Next, polymer spheres (having a diameter of from 30-400 nm) can be coated on the OSC compound and used as a mask for coating the metal mask layer, which is produced using one or more known methods, including lithography. Subsequently, the polymer beads are removed via solvent, heating, or adhesion to produce the grid. Finally, the collector layer is patterned on the OSC via lithography.

EXAMPLES

The following examples are put forth so as to provide those of ordinary skill in the art with a complete disclosure and description of how the materials, articles, and methods described and claimed herein are made and evaluated and are intended to be purely exemplary and are not intended to limit the scope of the description. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that may be used to optimize the product purity and yield obtained from the described process. Only reasonable and routine experimentation will be required to optimize such process conditions.

Example 1—Testing Device Fabrication

Figure 2A:
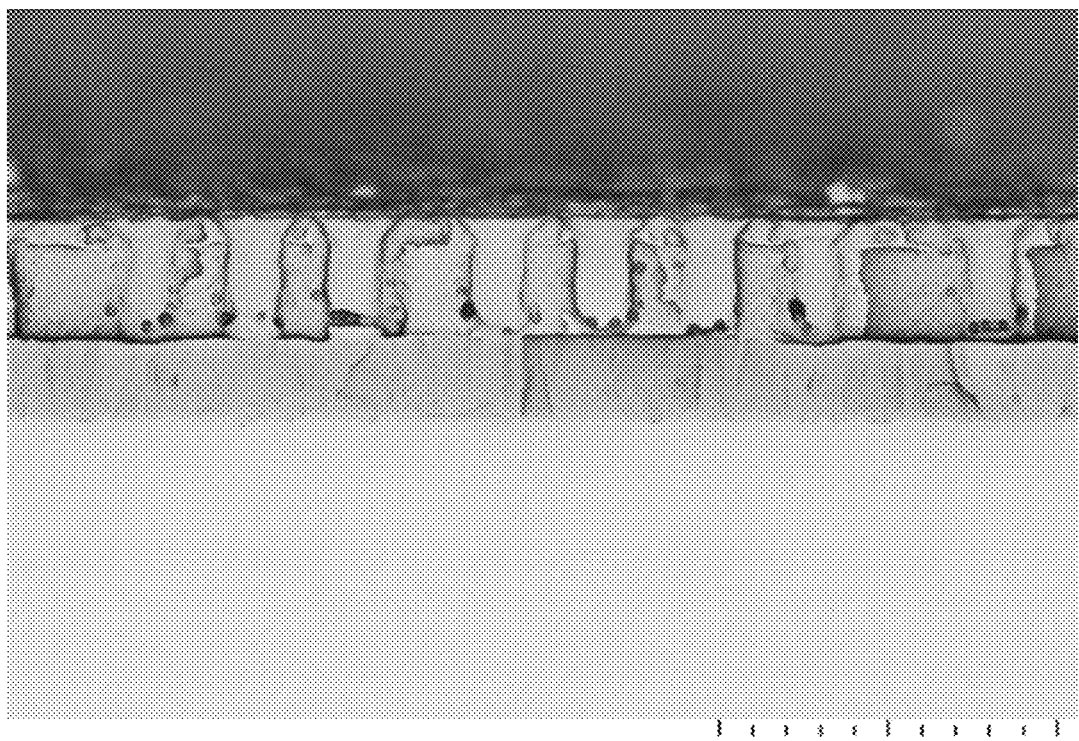
FIGS. 2A-2C illustrate a vertical sidewall of a sensor structure using a scanning electron microscopy (SEM) (FIGS. 2A and 2C) and a schematic of the gas sensor (FIG. 2B), according to some embodiments.
Figure 2B:
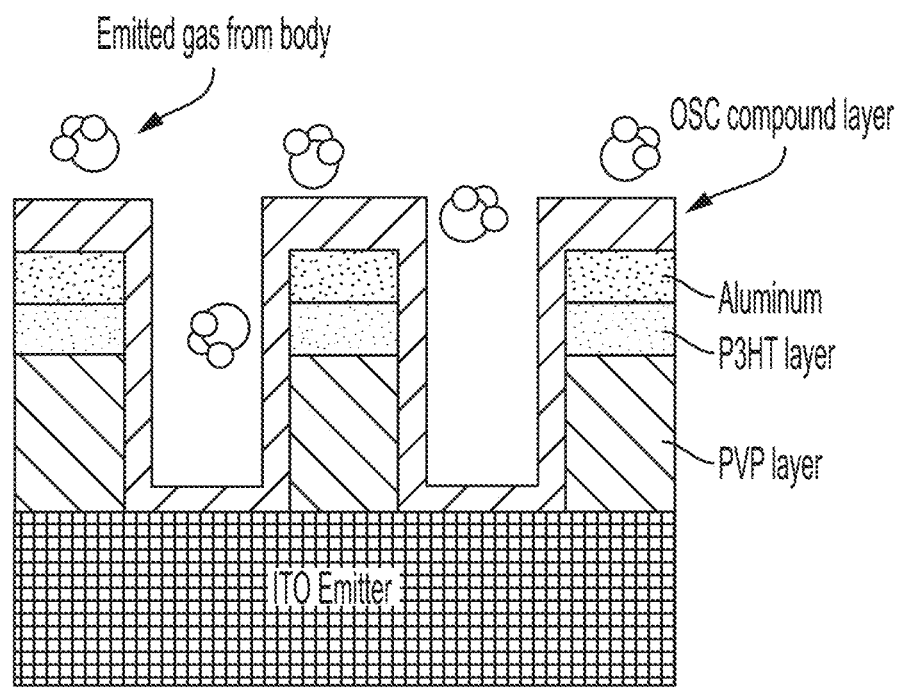
Figure 2C:
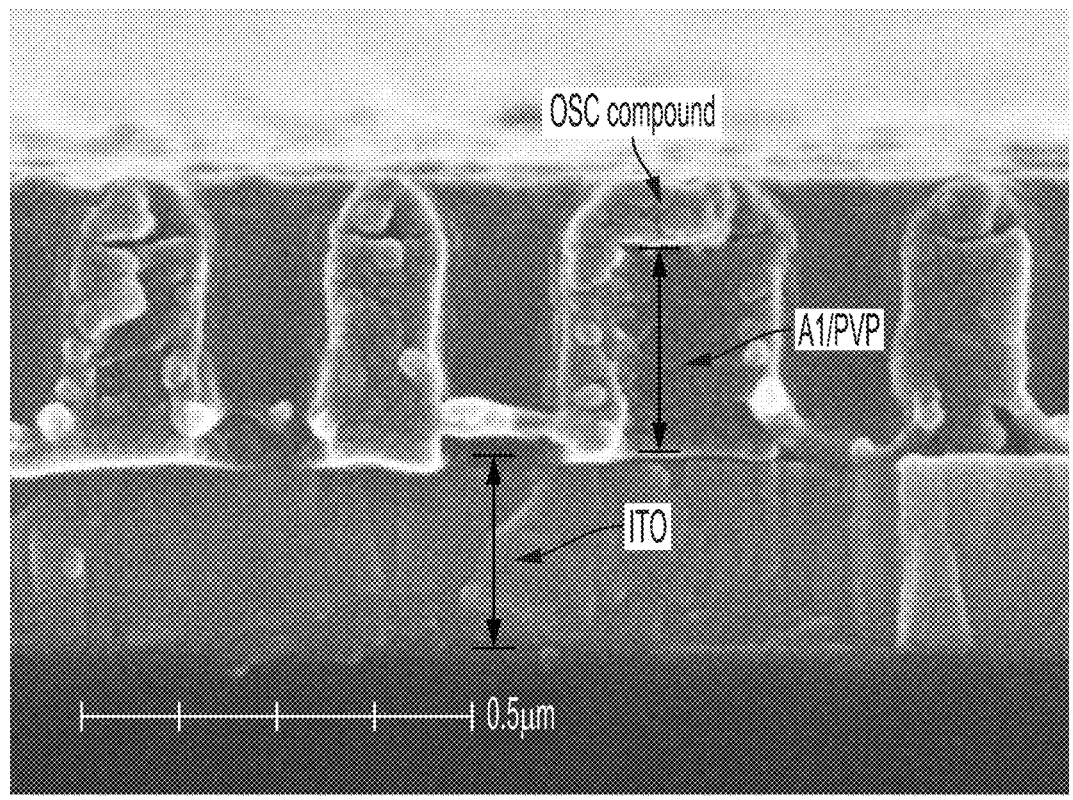

An example of a structure of a gas sensor with vertical nano-channels is shown in FIG. 1 and described above. FIGS. 2A-2C illustrate a vertical sidewall of a cylindrical channel (as shown by the cross-section in FIG. 1) covered with active OSC compounds. The vertical sidewalls of the sensor structure is imaged using SEM (FIGS. 2A and 2C) and schematically depicted in FIG. 2B. FIG. 2C is an enlarged version of FIG. 2A. SEM images are collected using a cold-field emission SEM (Hitachi SU-8010). Thickness of ITO emitter on the glass substrate is about 200 nm, thickness of the insulating poly(4-vinlphenol) (PVP) layer is 300 nm, thickness of the final active layer is about 60 nm. The active channel is on the vertical sidewall.

Three types of active OSC compounds were tested:

poly{4,8-bis[(2-ethylhexyl)oxy]benzo[1,2-b:4,5-b'] dithiophene-2,6-diyl-alt-3-fluoro-2-[(2-ethylhexyl) carbonyl]thieno[3,4-b]thiophene-4,6-diyl} (PTB7) (deposited with 0.5 wt. % chloroform solution)

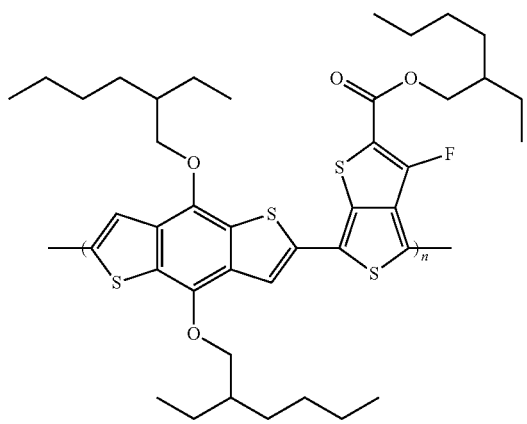 [SMILES: CCCCC(CC)COC(=O)c1sc2c(-c3cc4c(OCC(CC)CCCC)c5sc(C)cc5c(OCC(CC)CCCC)c4s3)sc(C)c2c1F]

2,6-Bis(trimethyltin)-4,8-bis(5-(2-ethylhexyl)thiophen-2-yl)benzo[1,2-b:4,5-b' ]dithiophene (PBDTTT-CT, or CT for simplicity) (deposited with 1 wt. % chloroform solution)

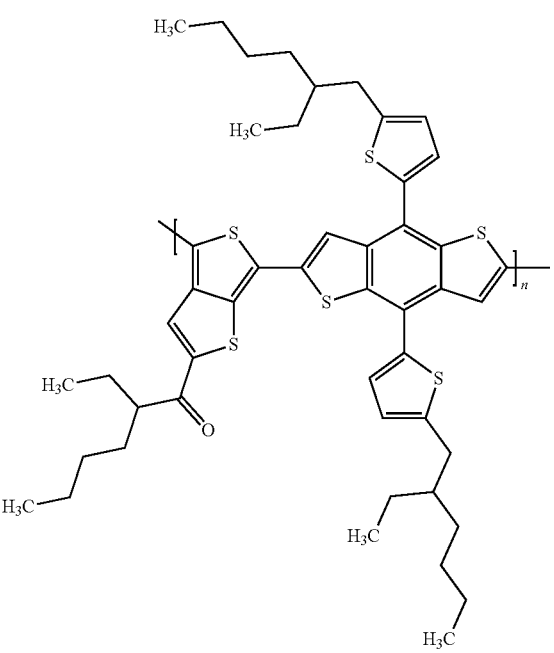

and poly[((3,7-bis(heptadecyl)thieno[3,2-b]thieno[2',3':4,5]thieno[2,3-d]thiophene)-2,6-diyl)-alt-((3,6-bis(thiophen-2-yl)-2,5-bis(8-octyl-octadecyl)pyrrolo[3,4-c]pyrrole-1,4(2H,5H)-dione)-5,5'-diyl)] (FT4X-Green, or FT4X for simplicity) (deposited with 0.5 wt. % xylene solution)

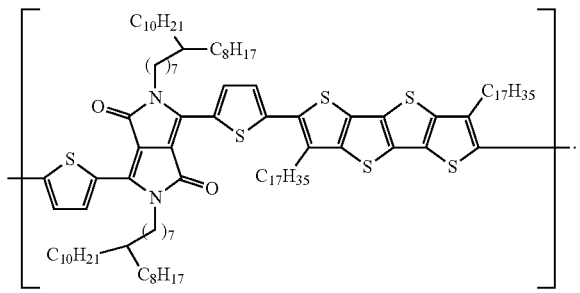

FT4X is a polymer comprising a diketopyrrolopyrrole (DPP) having N,N'-substitutents of two $C_8H_{15}$ ($C_8H_{17}C_{10}H_{21}$) groups, an intervening thiophene, and a fused thiophene having four fused rings ("FT4") with attached two $C_{17}H_{35}$ groups or chains as β-substituents (i.e., on the β-positions of the FT4 portion).

A generalized OSC compound fabrication procedure is as follows. The monomers and catalyst materials for each of PTB7, CT, and FT4X, respectively, are weighed into a flask and the solvent (chloroform for PTB7 and CT; xylene for FT4X) is added. Polymerization is then carried out at a predetermined time (e.g., 0.1-10 hrs, or 0.1-7.5 hrs, or 0.5-5 hrs) and temperature (e.g., 50-200° C., or 50-150° C., or 70-150° C.). In some examples, polymerization of PTB7 may be carried out for 10 min at 200° C. In some examples, polymerization of CT may be carried out for 10 min at 80° C. In some examples, polymerization of FT4X may be carried out for 60 min or 90 min at 130° C. The material is then precipitated, filtered, dried then extracted in a Soxhlet extractor to remove any residual monomers and catalyst species. Finally, the polymer is dissolved from the Soxhlet extractor, re-precipitated and dried under vacuum. The OSC compounds are used as the active material in vertical transistors with high output current density and a long lifetime without encapsulation.

As gas emitted from the body (target gas molecules) flow into the sensor, some portion will be adsorbed by the OSC compound layer. Charge transfer between the OSC compound and gas molecule may occur, causing a vertical electrical current output by the sensor. The gas sensor has a vertical channel with organic semiconductors, and in some examples, has a sensitivity of ammonia detection to as low as 30 parts-per-billion (ppb) using the electrical current responses. The gas sensor is also sensitive to aldehyde (e.g., comprising 7-9 carbon atoms) detection. Gas samples may be collected from various skin positions such as the hand (e.g., palm), forehead, forearm, chin, and elbow.

Example 2—Testing Device Characterization

As presented herein, vertical sensors are applied to unknown gases emitted from the human skin. Because of variations among different sensors, as well as variations of the same sensor at different times, ammonia gas with known concentration is used as the calibration gas. For a given unknown gas, the sensor uniquely responds with a current change percentage. The effective ammonia concentration is defined as the ammonia concentration which provides the same sensor current change percentage at the time of the measurement for the particular sensor. In other words, because unknown gases are emitted, sensors with different sensing material are also used and to compare the results with the different sensors, an "effective ammonia concentration" is used to describe the sensing result. The effective ammonia concentration is determined according to a sensor calibration curve, where sensor response is plotted as a function of ammonia concentration. For the characterizations shown herein, gas detection measurements are provided in terms of effective ammonia concentration (ppb) to cancel systematic variations of the sensor.

Figure 3:
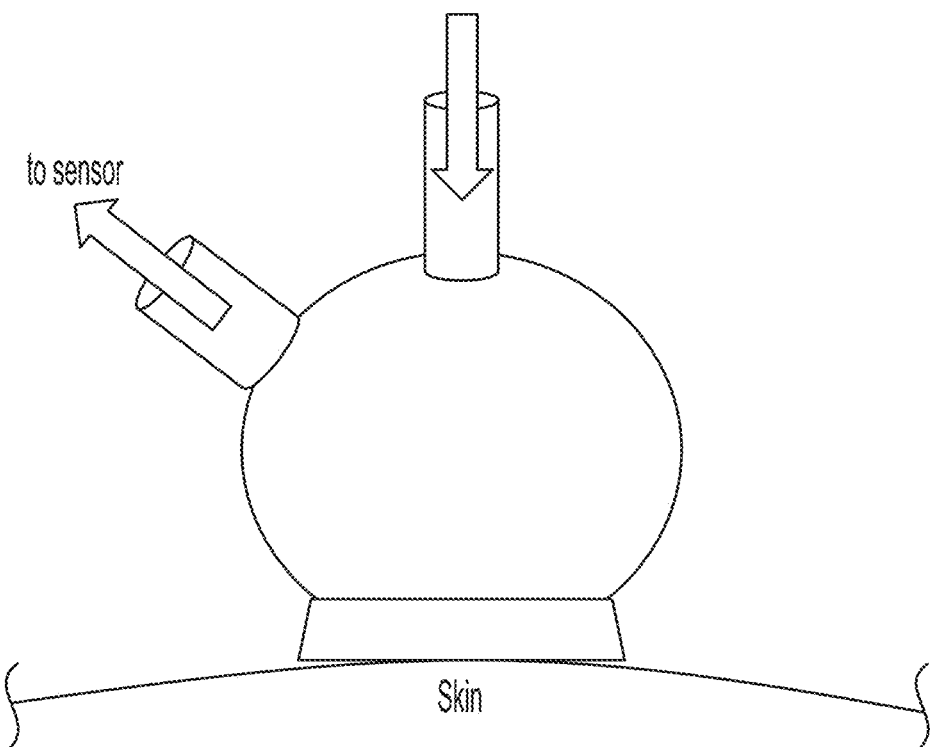
FIG. 3 illustrates a gas collection mechanism, according to some embodiments.

FIG. 3 illustrates a gas collection mechanism of the gas emitted from human skin. A glass enclosure covers the area of interest, with the enclosure comprising two tubes connected therein. As air is flown inward into the enclosure from a first tube, gas emitted from the skin is carried outward by the air through a second tube for characterization to a sensor chamber. Prior to entering the sensor chamber, the target gas molecules pass through a tube of sodium hydroxide solid to remove moisture. Target gas flow is driven by a pump connected to the sensor chamber, with the flow rate fixed at 500 cc/min. Electrical current remains at an air background level before the glass enclosure contacts the skin. Once the enclosure touches the skin, an airtight seal is formed above the skin such that the air flow carries the emitted skin gas through the second tube to the sensor chamber.

Current changes are due to the detected skin gas and the sensor response is defined as the percentage of change in 60 sec. Response of the sensor to several aldehydes are also measured (propanal, haptanal, octanal, and nonanal are purchased from Uni-Onward Corp.). Aldehyde liquids are first injected into a plastic bag (Tedlar bag from Kohan Instruments Co.) and then the bag is sealed and the liquids evaporate shortly. The aldehyde gas in the plastic bag is then pumped out and mixed with the air (entering through the first tube) with individually controlled flow rates for each aldehyde in order to vary aldehyde gas concentration. Skin gas is also analyzed by a gas chromatography-mass spectroscopy (GC-MS) system. GC-MS is conducted using an Agilent Model No. 6890-5972 device (35° C., hold 5 min then increase 15° C./min to 180° C., hold 10 min). The target gas molecules are first adsorbed on an inner surface of the winding column. Upon heating, different target gas molecules are released at different times. The skin gas for the GC is also collected by the glass enclosure, as in the case of the vertical sensor. Both air background and the skin gas are measured by the GC system in order to identify the real gas from the skin.

To further specify, response of the vertical sensor to ammonia in air is used as a calibration for other gases. If not specified, the OSC compound in the vertical sensor is PTB7. Current response (R) is defined as $\Delta I/I_0$, where $\Delta I$ is the change of current within 60 seconds and $I_0$ is the initial current before the flow of ammonia to the sensor chamber. The dependence of R on ammonia concentration is in ppb. Such ammonia response is used for further calibration as there is a variation among devices and gradual decay through time for an individual device.

Figure 4:
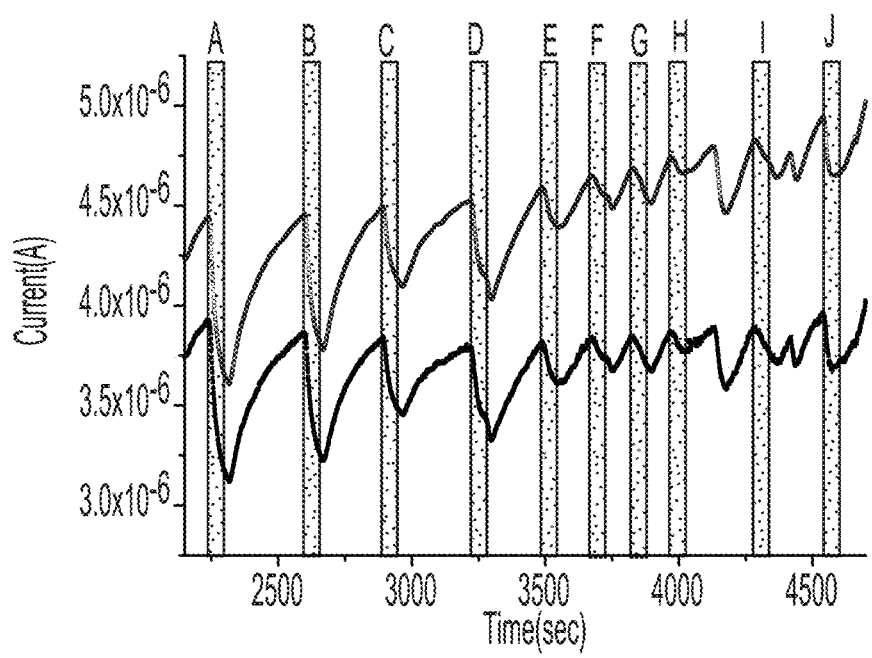
FIG. 4 illustrates a plot of measured current of a vertical sensor described herein as a function of time when collecting gas from various parts of the human body, according to some embodiments.

FIG. 4 illustrates how the electrical current of the sensor is altered when measuring gas emitted from the human skin at various positions. Body parts measured are the left palm (A), right palm (B), back of left hand (C), back of right hand (D), left forearm (E), right forearm (F), left elbow (G), right elbow (H), chin (I), and forehead (J). As described above, the skin gas is collected by a glass enclosure which covers the skin. There are two tubes for the carrier air to flow, one as an inlet to the enclosure, and one as an outlet to the sensor chamber. A constant flow rate of 500 cc/min is maintained. From FIG. 4, the current drops at the moment when the glass enclosure covers the skin and begins to recover as the enclosure leaves the skin. Thus, a clear and strong drop in the current is observed when skin gas flows through the sensor chamber for certain body positions like the palm (A and B) or forehead (J). For other body positions, such as the forearms (E and F) and elbows (G and H), the response is very weak. The response of the skin gas is represented by an effective ammonia concentration which gives the same response in percentage for the same device at the same time.

Figure 5:
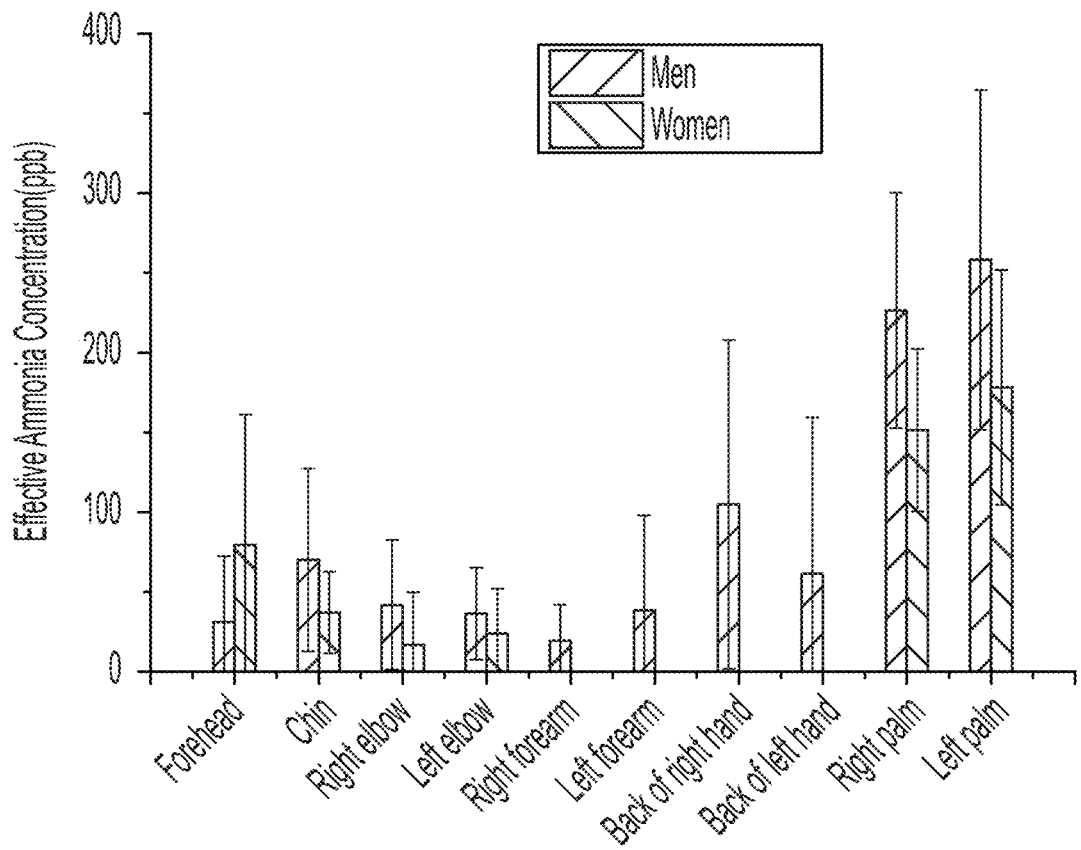
FIG. 5 illustrates a plot of measured ammonia concentration from various parts of the human body for both males and females, according to some embodiments.

This current response is confirmed by FIG. 5, which illustrates a plot of measured ammonia concentration from various parts of the human body for both males and females (with mean and standard deviation for men and women). In other words, the vertical sensor was used to measure the response of the gas emitted from skin at various body positions for eight (8) healthy volunteers, including four (4) men and four (4) women between the ages of 20 and 30, with an average age of twenty-three (23) for both men and women. As the trend in FIG. 4, a strong effective ammonia concentration signal was detected for the palm in both men and women. Chin, forehead, and elbow show moderate-to-low signals for both sexes. And while men have signals from hand backs and forearms, signals from these positions are barely detectable for women.

Figure 6:
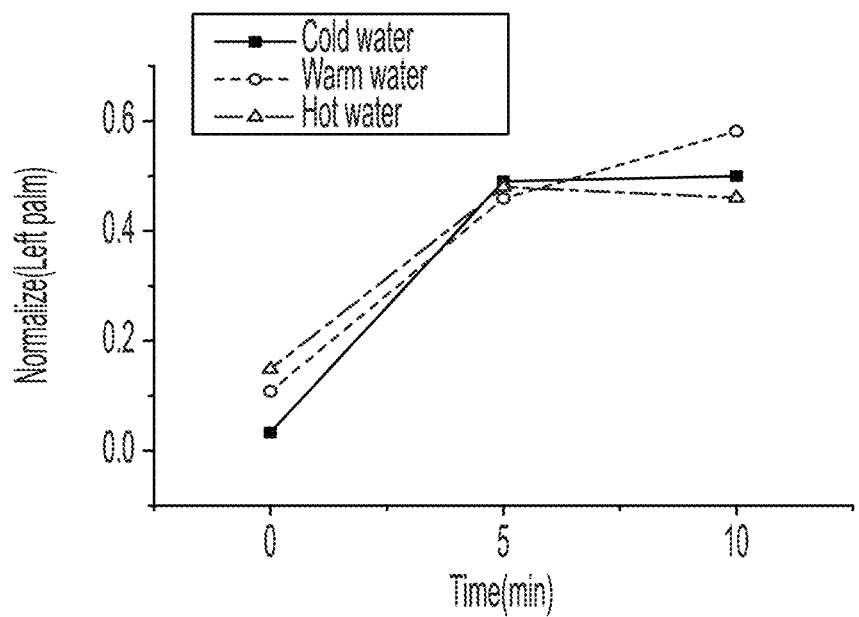
FIG. 6 illustrates a plot of signal recovery after washing hands with cold, warm, and hot water, according to some embodiments.

FIG. 6 illustrates a plot of signal recovery after washing hands with cold, warm, and hot water, according to some embodiments. Because palm of the hand show a particularly large signal, attention is given to understand effects of hand washing. Water is used to wash the hands and the normalized recovery of the response as a function of time after washing is shown in FIG. 6. As expected, immediately after washing response is low, regardless of washing water temperature. However, after 5 minutes, response rises to its steady state value.

Because the vertical sensor described herein is very sensitive to ammonia, it is important to know if the skin gas is dominated by ammonia. Sensitivity to ammonia is tested and compared using three OSC materials: organic vertical transistors are formed as described herein with organic semiconductor layers comprising PTB7, CT, and FT4X. For any given kind of molecule (in this case, ammonia), unique relative strengths of adsorption and reaction are observed with each of the three OSC materials. Put together, the ratio among the three responses can therefore serve as a fingerprint, or identifier, of the type of molecule. Different molecules, in general, will have different ratios.

Figure 8:
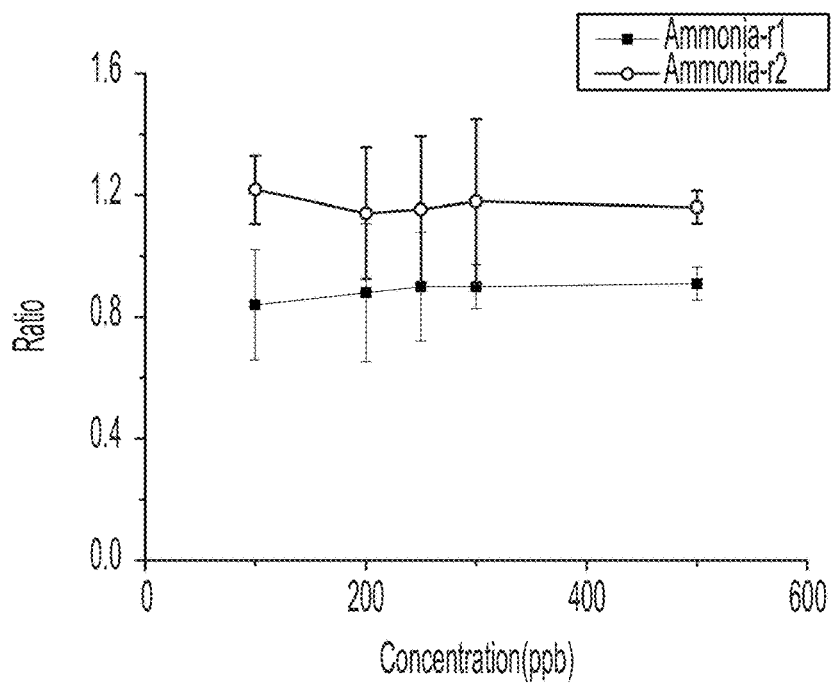
FIG. 8 illustrates a mean and standard deviation for ammonia ratios at various concentrations, according to some embodiments.
Figure 10:
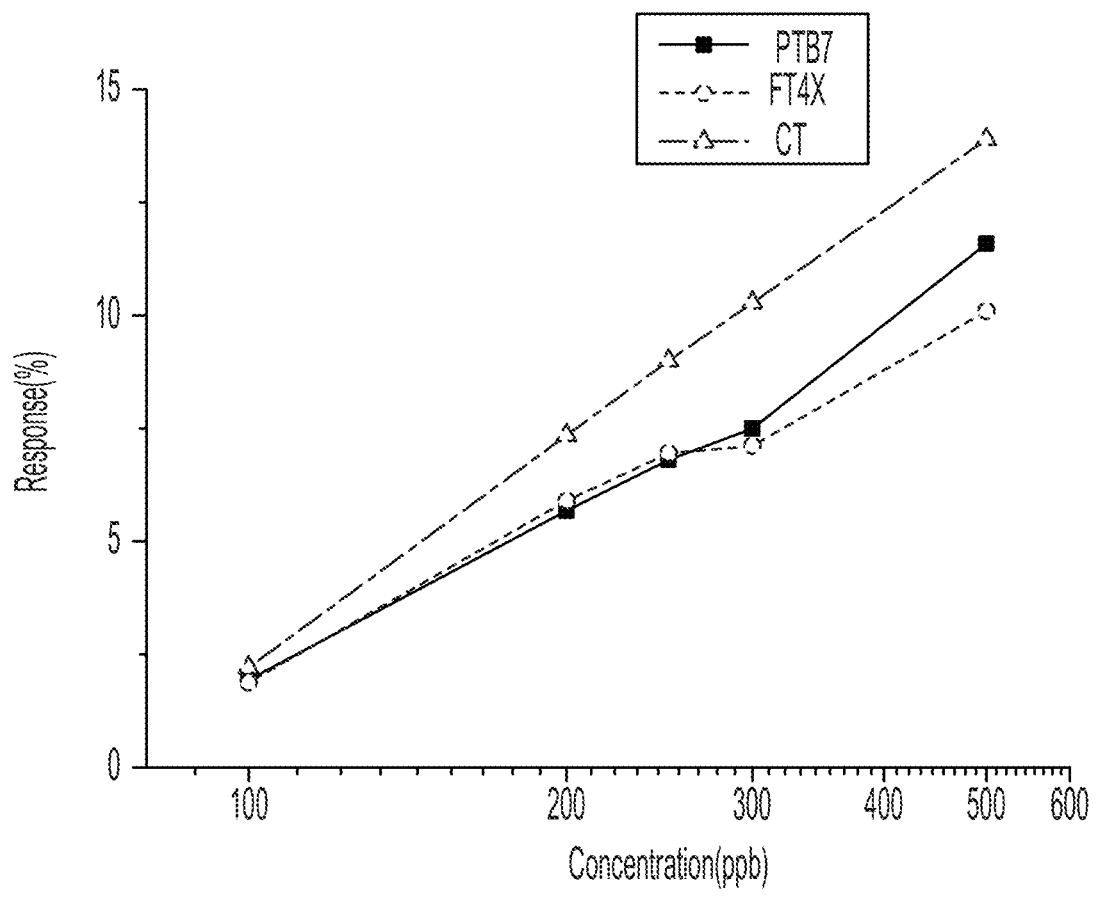
FIG. 10 illustrates a plot of gas sensor response signal as a function of ammonia concentration when the gas sensor comprises organic semiconductor layers having PTB7, CT, and FT4X.

Here the three OSC materials are PTB7, CT, and FT4X, with the response of PTB7 being the standard. FIG. 8 illustrates a mean and standard deviation for ammonia ratios at various concentrations, according to some embodiments. The ratio for the palm are also shown in FIG. 8 for a total of twelve (12) data points collected from various days. Roughly, $r_1$ is 1.2 and $r_2$ is 0.9. Whereas there is no significant difference in $r_1$, the $r_2$ values for palm and ammonia are significantly different. Thus, palm gas is not dominated by ammonia. FIG. 10 illustrates a plot of gas sensor response signal as a function of ammonia concentration when the gas sensor comprises organic semiconductor layers having PTB7, CT, and FT4X. The ratio of the FT4X response to the PTB7 response is indicated as $r_\alpha$, and the ratio of the CT response to the PTB7 response is indicated as $r_\beta$. For 300 ppb, $r_\alpha$ is 1.1 and $r_\beta$ is 0.5; for 500 ppb, $r_\alpha$ is 1.1 and $r_\beta$ is 0.6; for 700 ppb, $r_\alpha$ is 1.1 and $r_\beta$ is 0.5.

Figure 9A:
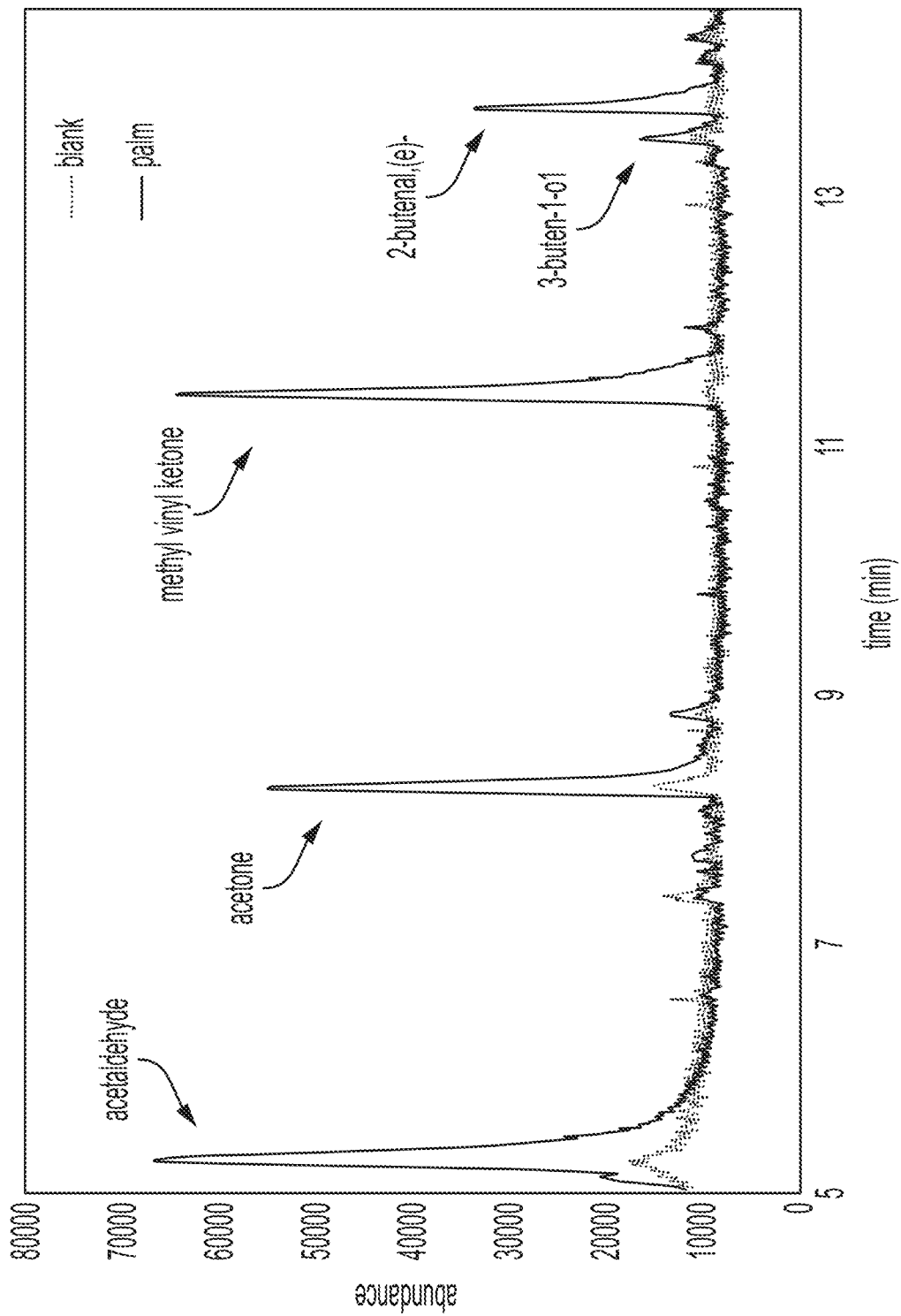
FIGS. 9A-9C illustrate gas chromatography-mass spectroscopy (GC-MS) plot for the detection of emitted aldehyde skin gas, according to some embodiments.
Figure 9B:
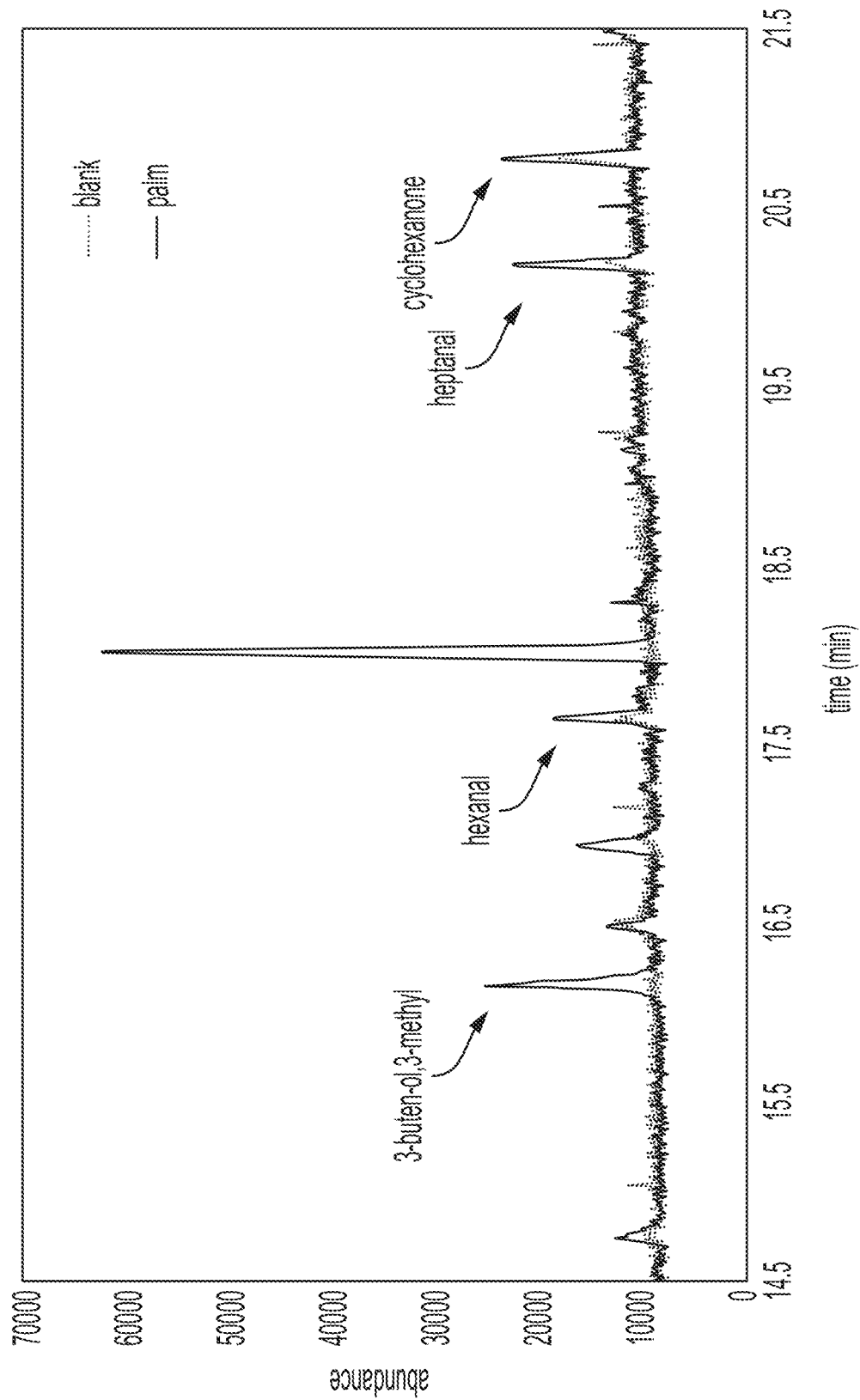
Figure 9C:
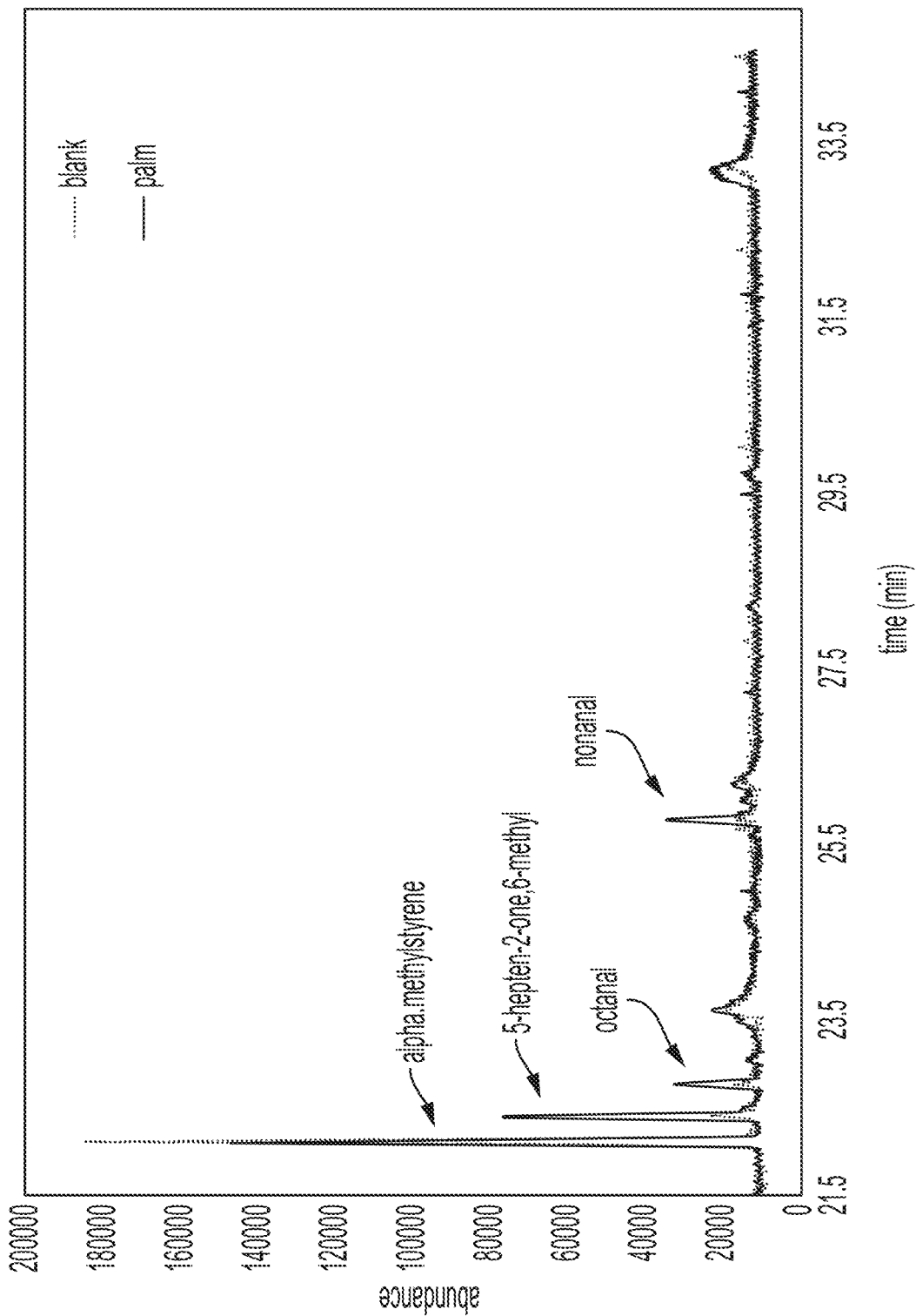

From FIG. 8, it was shown that the chemical composition of the skin gas is one not dominated by ammonia. GC-MS is used to study the skin gas (see above) in FIGS. 9A-9C. Using the glass enclosure, skin gas can be pumped to the GC directly with a nitrogen background. Molecules with molecular weight lower than $M_w$=33 were not detected by GC. Different molecules are released from the GC column under heating at different times. As the abundance is plotted against time in minutes there are several peaks, though a portion appear in the air control as part of the system background. Substantive signals include acetone and some aldehydes with 7 to 9 carbon atoms. The vertical sensor has a weak response for acetone. Aldehyde is therefore considered as a potential candidate which contributes to the sensor response from the skin gas.

Figure 7:
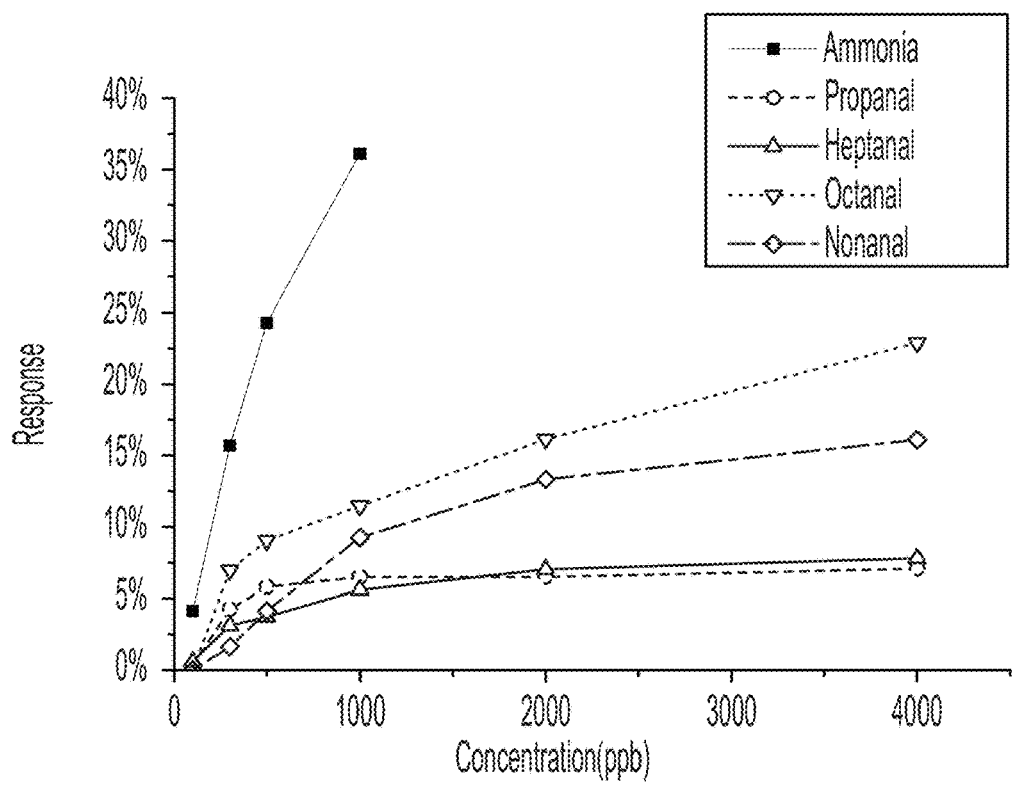
FIG. 7 illustrates a plot of sensor response sensitivity as a function of concentration for various chemical compounds, according to some embodiments.

FIG. 7 illustrates a plot of sensor response sensitivity as a function of concentration for various chemical compounds, according to some embodiments. While the gas sensors described herein are designed to detect ammonia, FIG. 7 discloses that other types of chemical compounds are also detectable, such as various aldehydes. FIG. 7 shows that ammonia detection requires relatively small quantities of ammonia (less than 1000 ppb). Propanal and heptanal exhibit the weakest sensor response signal, even at concentrations greater than 3000 ppb (>5% response), while octanal and nonanal detection response steadily increases with concentration.

Thus, as presented herein, improved OTFT devices having high relative current density at low voltages are disclosed.

Advantages

New applications of the OSC materials include vertical sensor devices which are able to detect gas emitted from skin. This application may be potentially used with mobile devices to monitor health risks and provide dynamic feedback of daily health information. Advantages include organic semiconductors which (1) are P-type and/or N-type materials which can be solution-processed into vertical designed structures; (2) may be polymers, small molecules, or combinations thereof; and (3) have thiophene, fused thiophene and other aromatic structures as donor-acceptor dipole molecule and polymers.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. The indefinite article "a" or "an" and its corresponding definite article "the" as used herein means at least one, or one or more, unless specified otherwise.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be apparent to those skilled in the art that various modifications and variations can be made without departing from the spirit or scope of the claimed subject matter. Accordingly, the claimed subject matter is not to be restricted except in light of the attached claims and their equivalents.

The invention claimed is:

1. A device for analyzing gas emitted from skin, comprising:
    an enclosure for collecting the gas emitted from skin, the enclosure comprising:
        an inlet through which a carrier gas is flown; and
        an outlet through which the carrier gas and the gas emitted from skin is flown into a vertical gas sensor,
    wherein the vertical gas sensor comprises:
        a substrate;
        a collector layer;
        an emitter layer positively biased relative to the collector;
        a metal grid comprising a metal layer having openings, the metal grid located in between, but not in direct contact with, the collector and emitter; and
        an organic semiconductor (OSC) layer located in between the collector and emitter,
    wherein the OSC layer comprises (a) soluble OSC small molecules and/or (b) an OSC polymer with the structure:

(I)

wherein each D is an independently selected conjugated electron donating aromatic or heteroaromatic group having from 5 to 50 backbone atoms and each D group is optionally substituted with one or more electron donating substituents or electron withdrawing substituents, provided that even when substituted the electronic character of each D is electron donating; each A is an independently selected conjugated electron accepting aromatic or heteroaromatic group having from 5 to 50 backbone atoms or an ethenylene group substituted with one or two electron withdrawing substituents, each A being optionally substituted with one or more electron donating substituents or electron withdrawing substituents provided that even when substituted the electronic character of each A is electron accepting; each of a and b is an integer from 1 to 4, and n is an integer from 2 to 10,000.

2. The device of claim 1, wherein each of the openings has a length along its longest dimension of from about 50 nm to about 800 nm.

3. The device of claim 1, wherein the vertical gas sensor further comprises:
    an insulating layer positioned between the emitter layer and the metal grid.

4. The device of claim 3, wherein the insulating layer is polyvinylpyrrolidone (PVP).

5. The device of claim 3, wherein at least the insulating layer and the emitter layer are patterned to form vertical nano-channels configured to adsorb the gas emitted from skin and wherein the OSC layer is disposed in the vertical nano-channels.

6. The device of claim 1, wherein the OSC small molecules include at least one of:

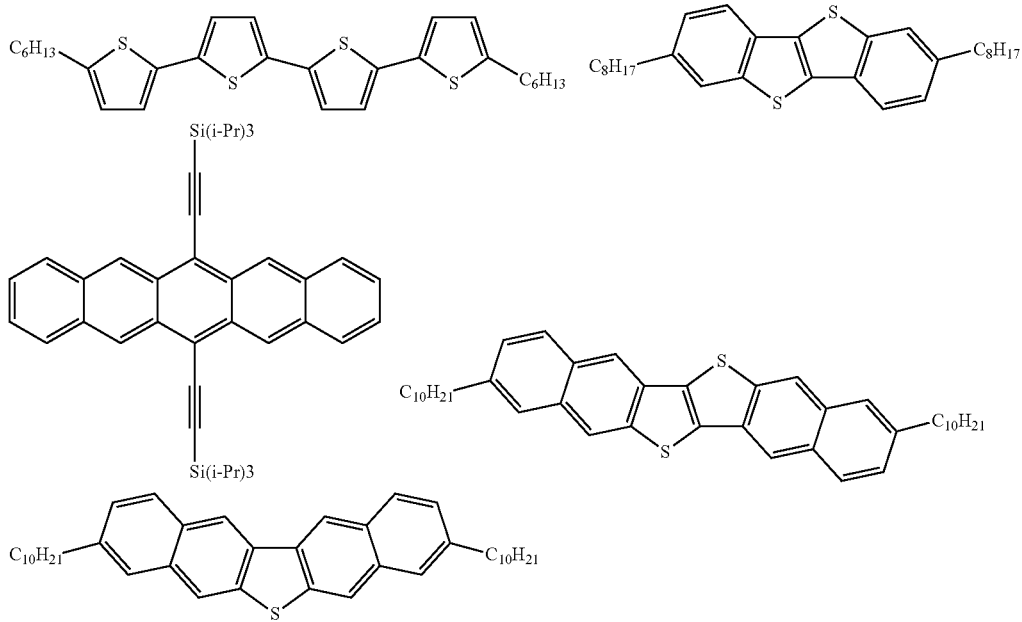

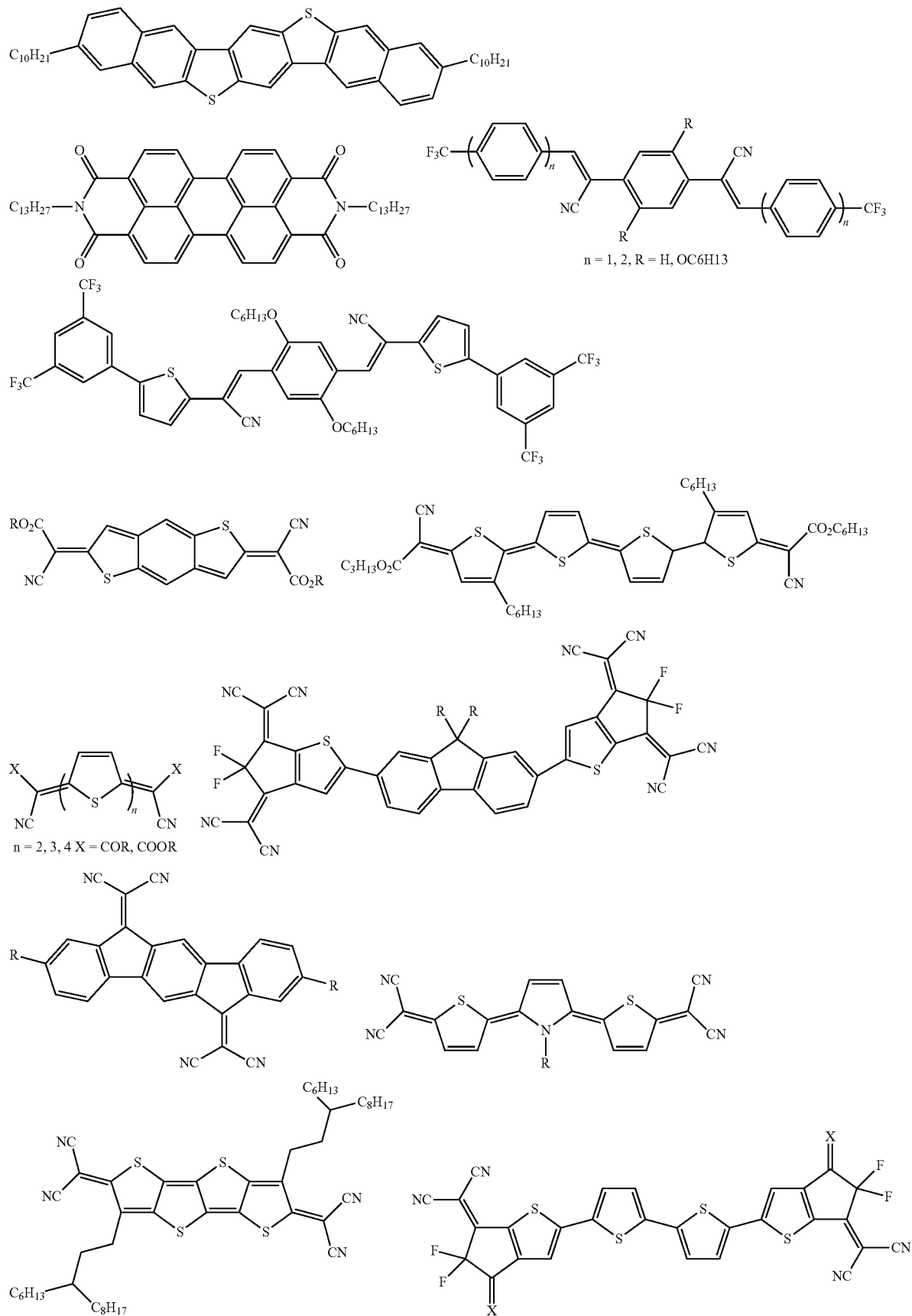

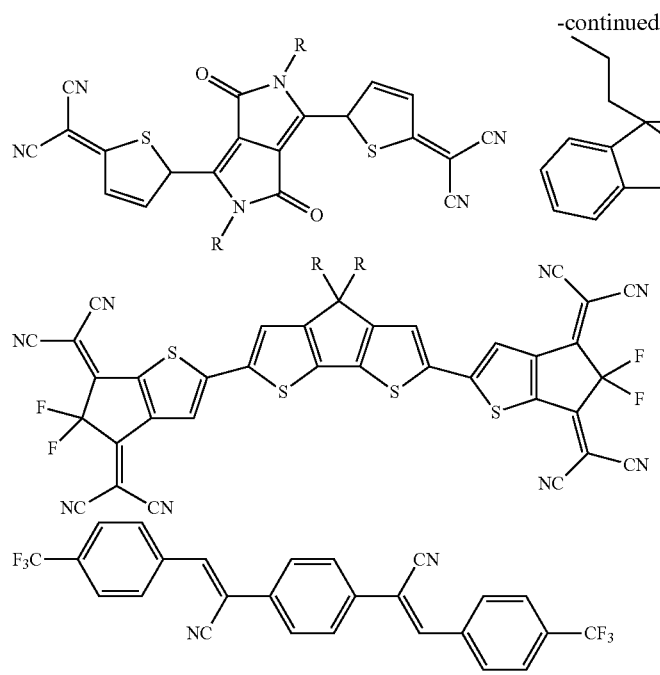
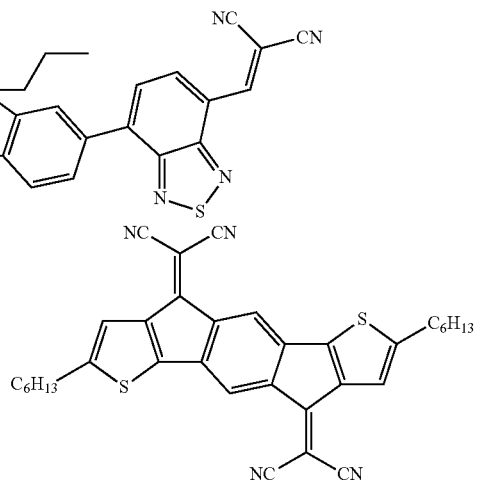
7. The device of claim 1, wherein each D is independently one of:
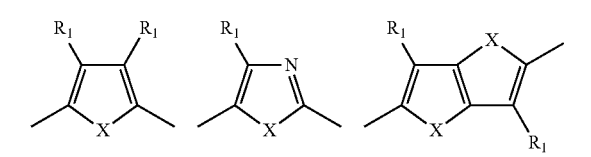
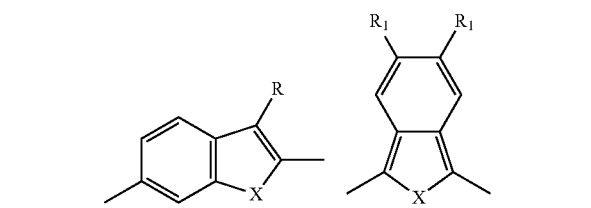
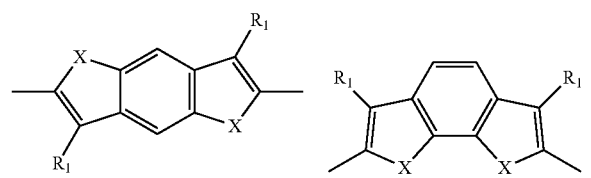
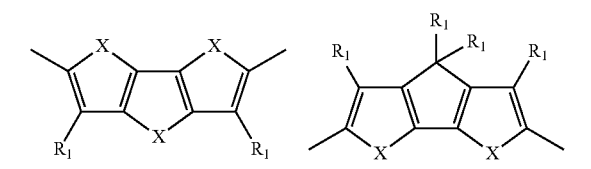
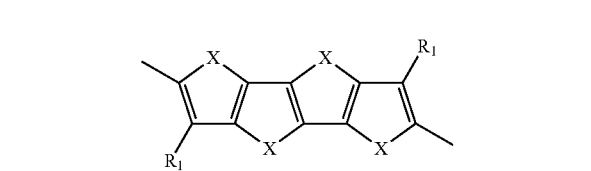
-continued
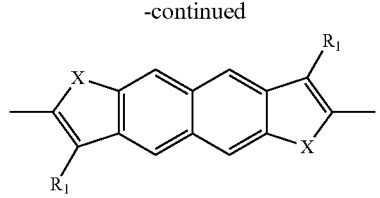
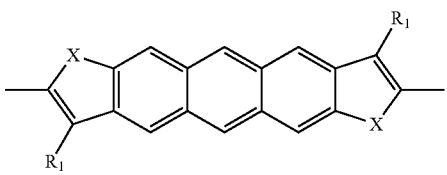
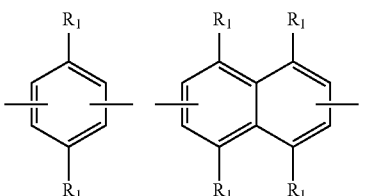
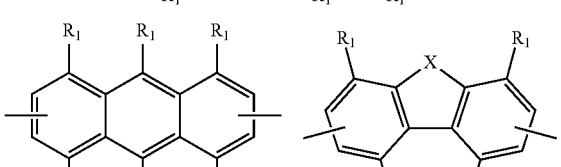
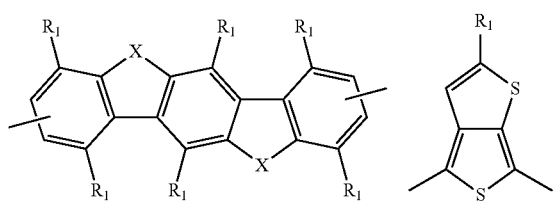

63

-continued

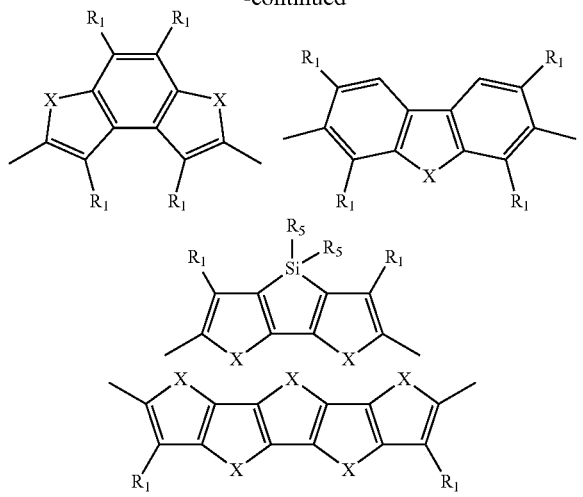

wherein each x is independently $NR_6$, S, Se, or O; each $R_1$ is independently hydrogen, $C_1$-$C_{40}$ alkyl, $C_1$-$C_{40}$ alkenyl, $C_1$-$C_{40}$ alkynl, $C_1$-$C_{40}$ alkoxy, $C_1$-$C_{40}$ cycloalkyl, $C_1$-$C_{40}$ aryl, $C_1$-$C_{40}$ heteroaryl, $C_1$-$C_{40}$ heterocycloalkyl, $C_1$-$C_{40}$ conjugated group, any of which may be optionally substituted, or halo; each $R_5$ is independently hydrogen, $C_1$-$C_{40}$ alkyl, $C_1$-$C_{40}$ alkenyl, $C_1$-$C_{40}$ alkoxy, $C_1$-$C_{40}$ cycloalkyl, $C_1$-$C_{40}$ aryl, $C_1$-$C_{40}$ heteroaryl, or $C_1$-$C_{40}$ conjugated group, any of which may be optionally substituted; and each $R_6$ is independently hydrogen, $C_1$-$C_{40}$ alkyl.

8. The device of claim 1, wherein each A is independently one of:

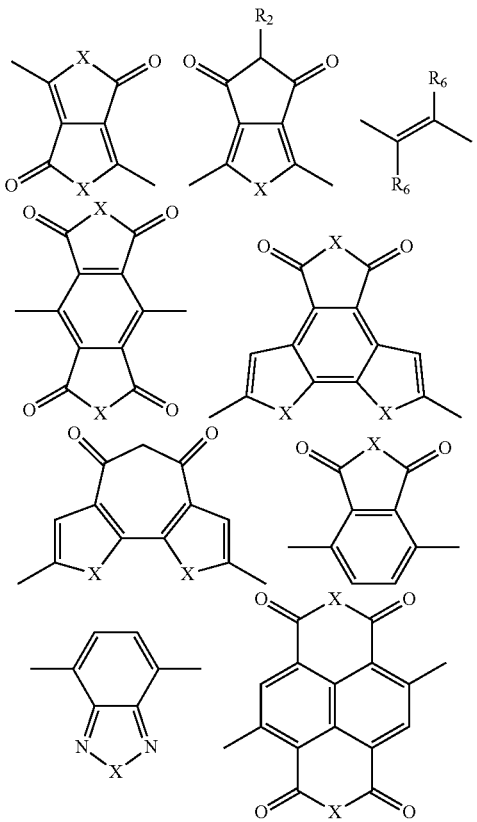

64

-continued

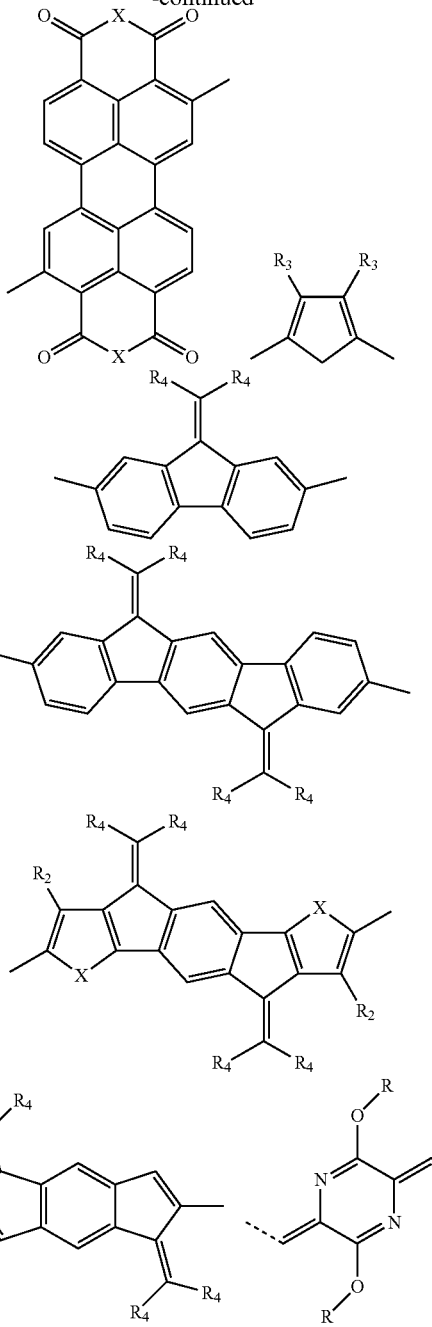

wherein each x is independently $NR_5$, S, Se, or O; each $R_2$ is independently hydrogen, $C_1$-$C_{40}$ alkyl, $C_1$-$C_{40}$ alkenyl, $C_1$-$C_{40}$ alkynl, $C_1$-$C_{40}$ alkoxy, $C_1$-$C_{40}$ cycloalkyl, $C_1$-$C_{40}$ aryl, $C_1$-$C_{40}$ heteroaryl, $C_1$-$C_{40}$ heterocycloalkyl, $C_1$-$C_{40}$ conjugated group, any of which may be optionally substituted, or halo; each $R_3$ is independently hydrogen, $C_1$-$C_{40}$ alkyl, $C_1$-$C_{40}$ alkenyl, $C_1$-$C_{40}$ alkoxy, $C_1$-$C_{40}$ cycloalkyl, $C_1$-$C_{40}$ aryl, $C_1$-$C_{40}$ heteroaryl, or $C_1$-$C_{40}$ conjugated group, any of which may be optionally substituted; each $R_4$ is independently hydrogen, $C_1$-$C_{40}$ alkyl, cyano, ester, or carboxylic acid, and each $R_6$ is independently hydrogen, $C_1$-$C_{40}$ alkyl, cyano, ester, or carboxylic acid.

9. The device of claim 7, wherein one or more of $R_1$, $R_2$, $R_3$, $R_4$, and $R_6$ is an optionally substituted $C_{15}$-$C_{35}$ alkyl.

10. The device of claim 9, wherein one or more of $R_1$, $R_2$, $R_3$, or $R_4$ is an optionally substituted $C_{15}$-$C_{35}$ alkyl having at least one branching point.

11. The device of claim 10, wherein one or more of $R_1$, $R_2$, or $R_3$ can be optionally substituted $C_{15}$-$C_{35}$ alkyl.

12. The device of claim 11, wherein each $R_1$ or $R_2$ is independently an optionally substituted $C_{15}$-$C_{35}$ alkyl.

13. The device of claim 12, wherein each $R_1$ or $R_2$ is independently an optionally substituted $C_{15}$-$C_{35}$ alkyl having at least one branching point.

14. The device of claim 13, wherein each $R_1$ or $R_2$ is independently an optionally substituted $C_{15}$-$C_{35}$ alkyl having at least one branching point, where the branching point is at least 4 carbons from the base molecule.

15. The device of claim 1, wherein the OSC layer comprises an OSC polymer including at least one of:

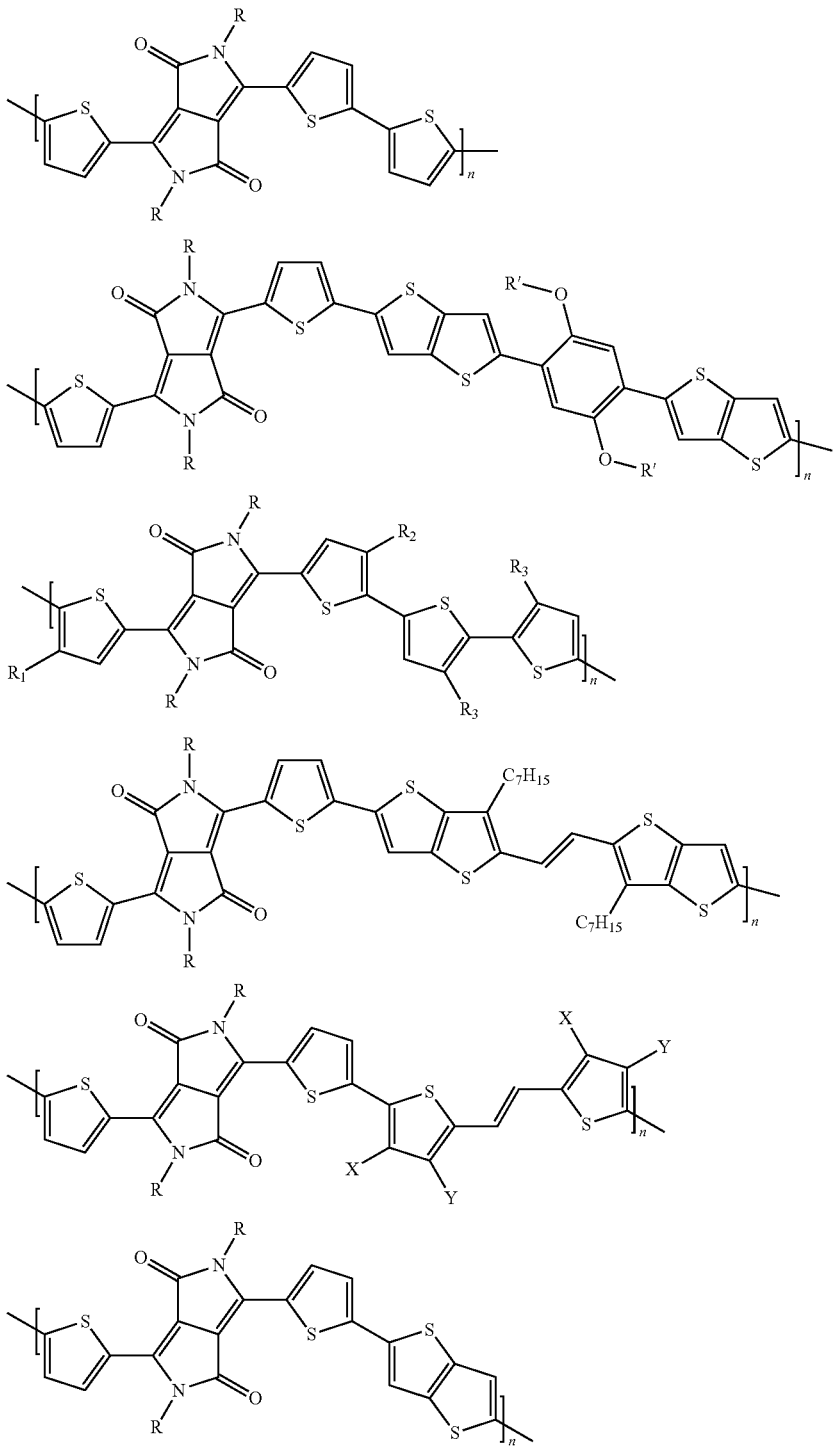

-continued
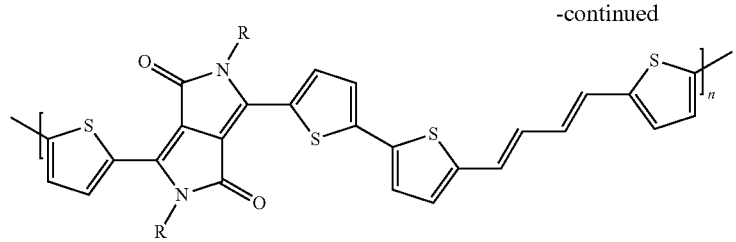
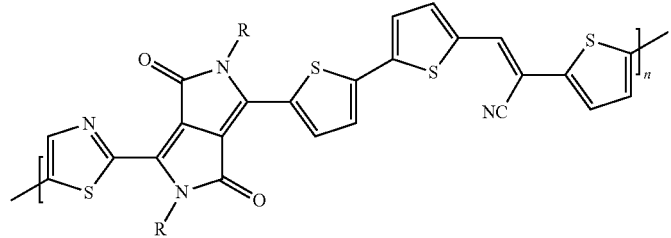
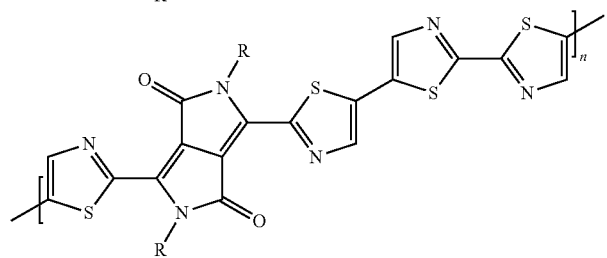
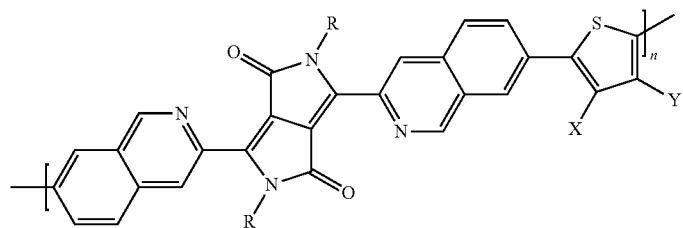
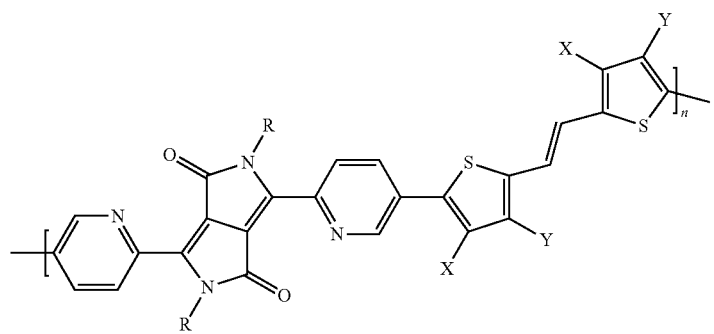
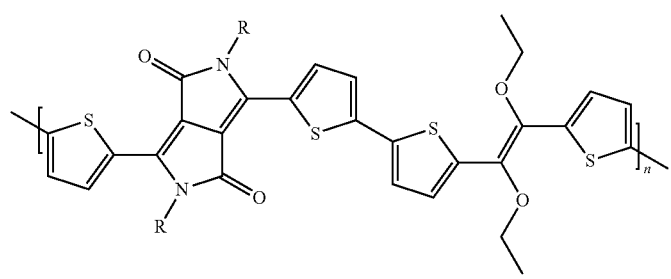

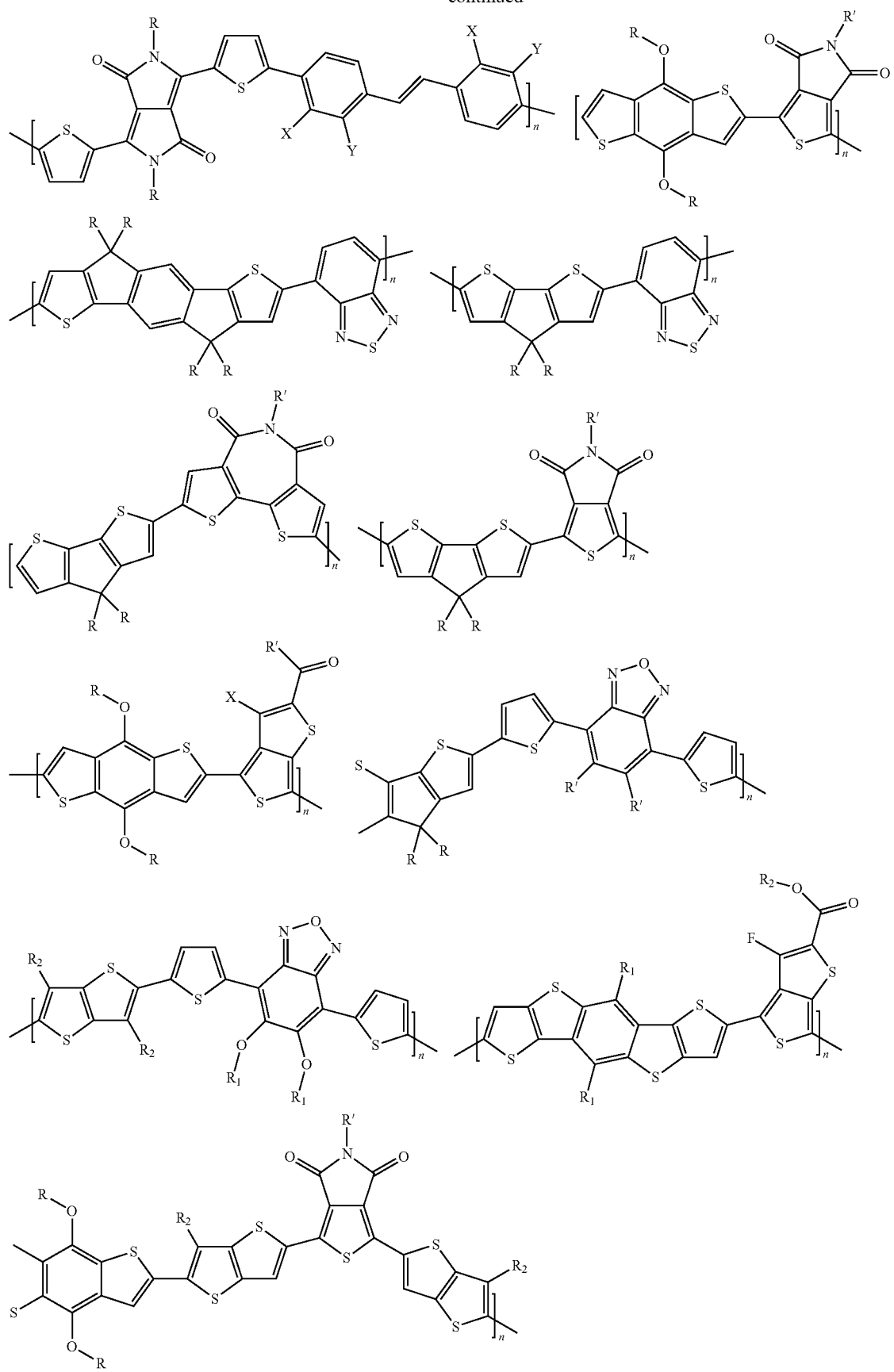

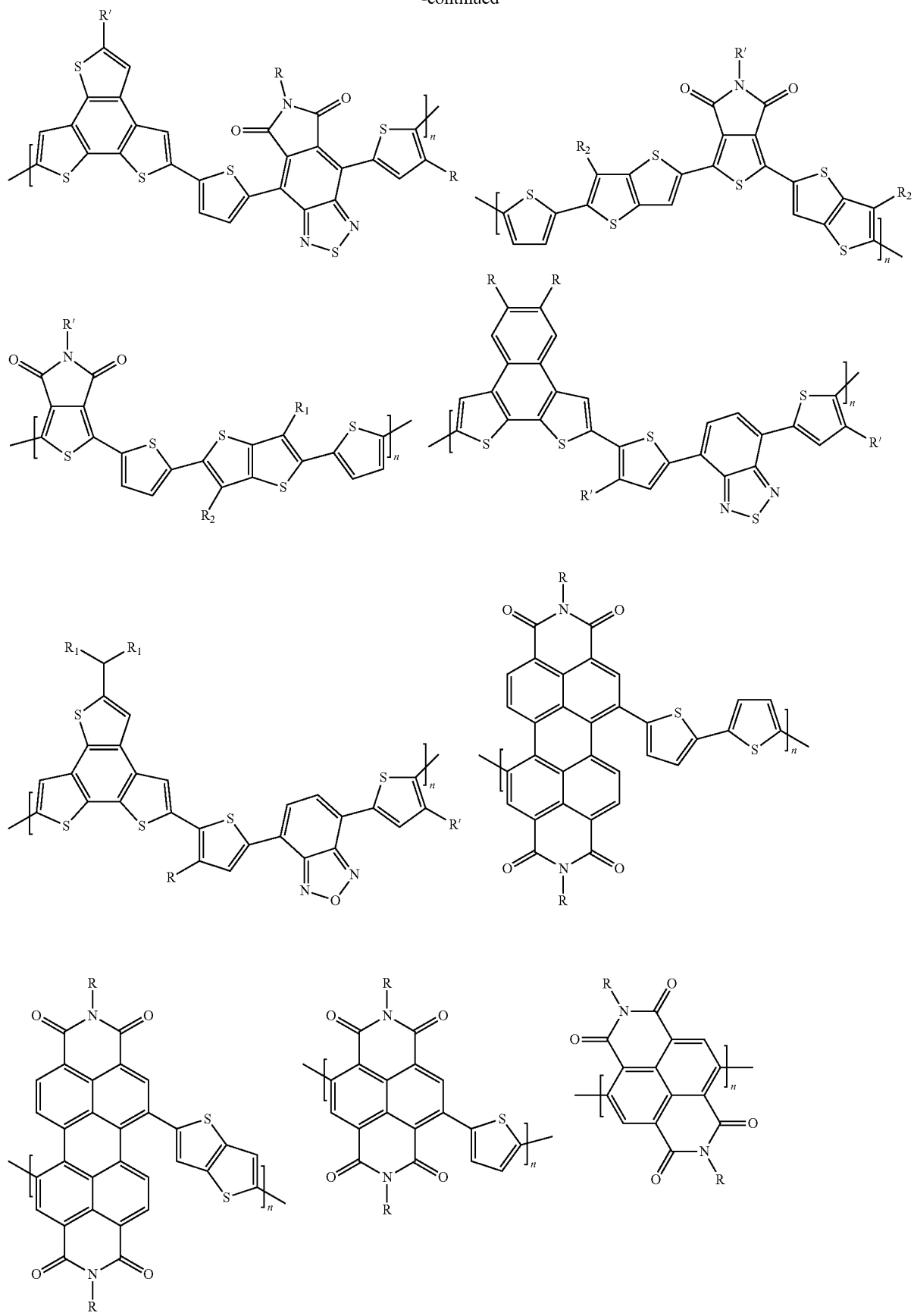

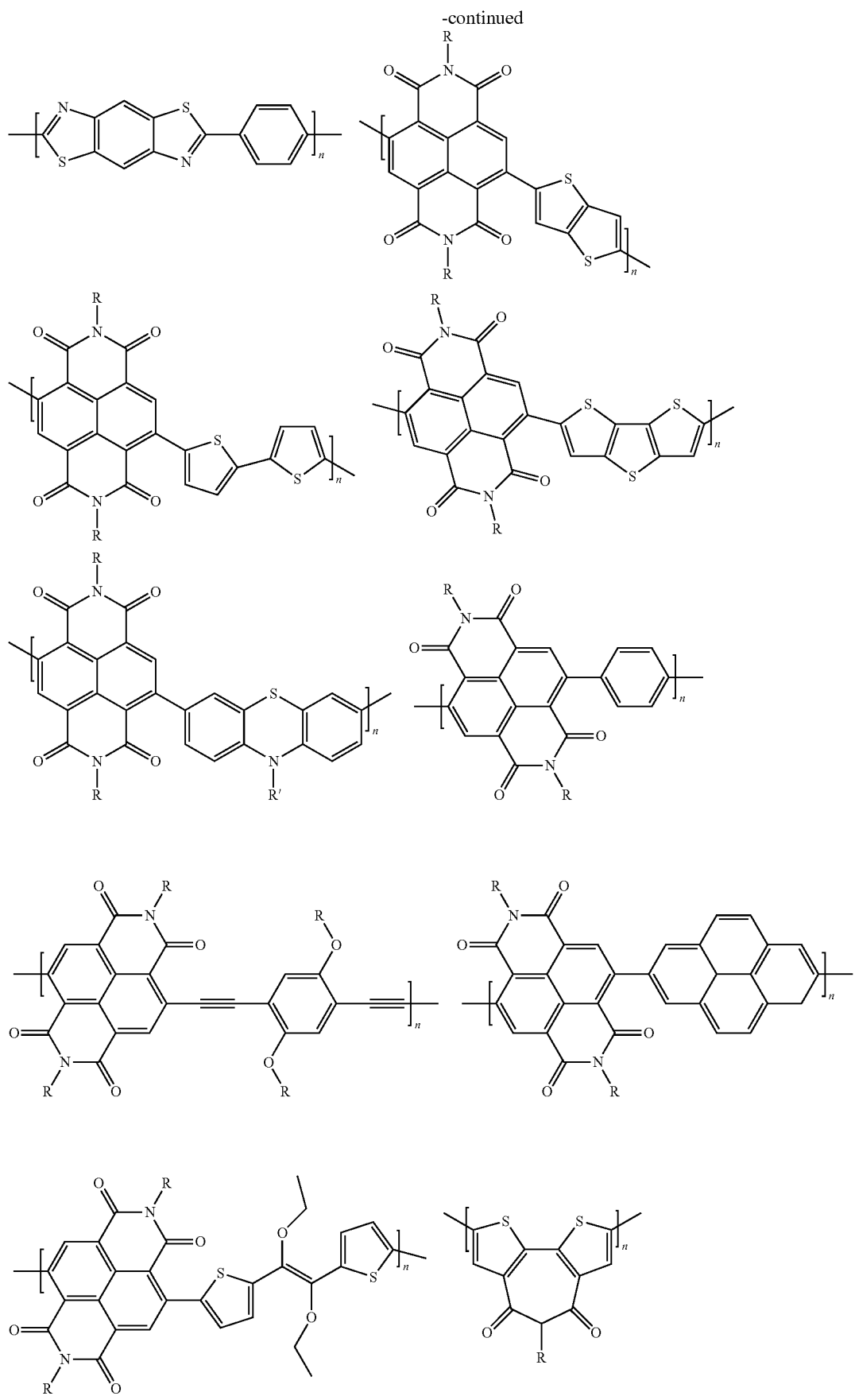

-continued
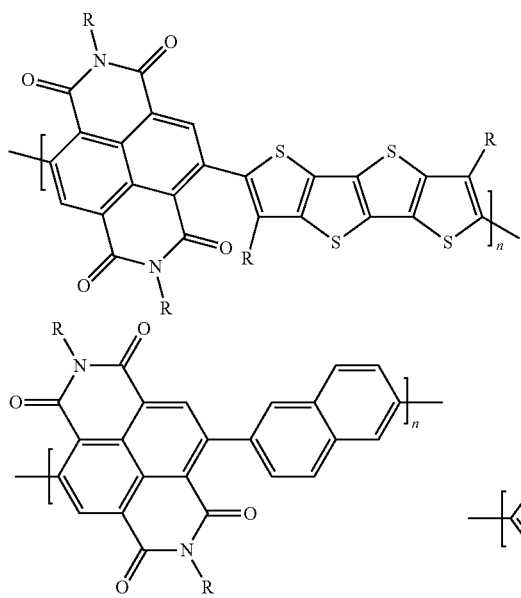
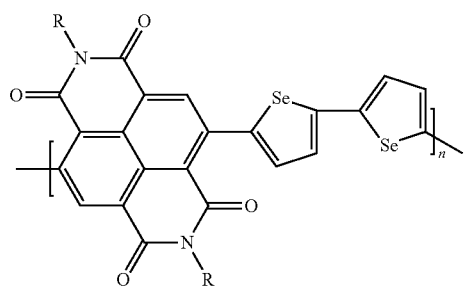
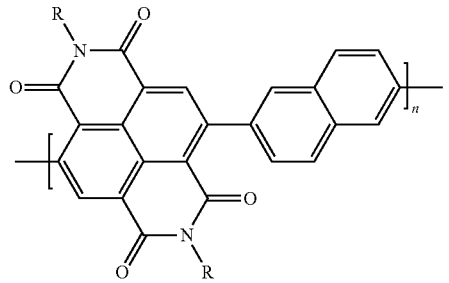
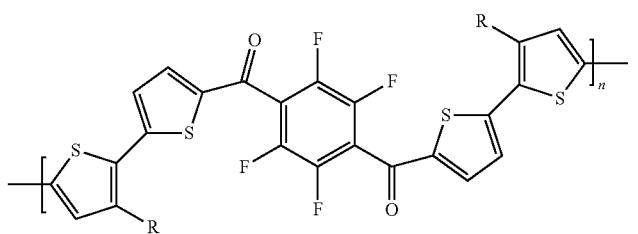
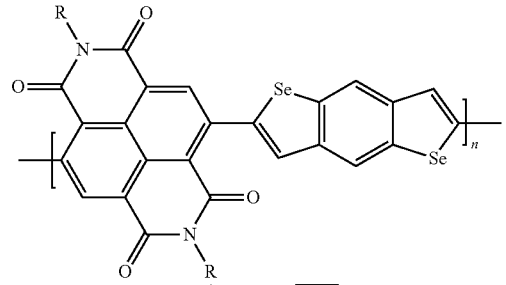
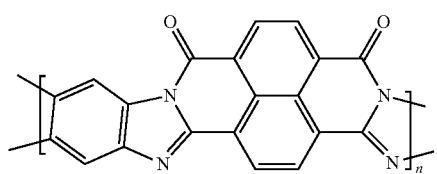
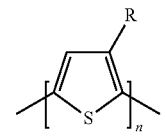
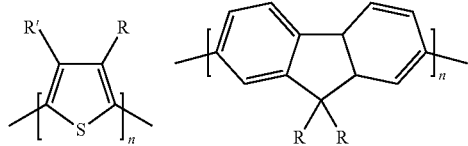
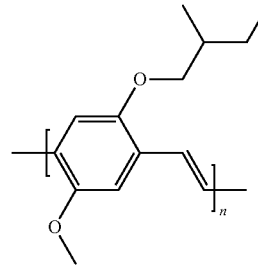
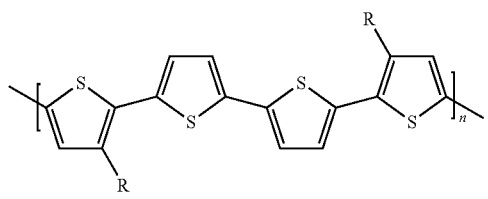
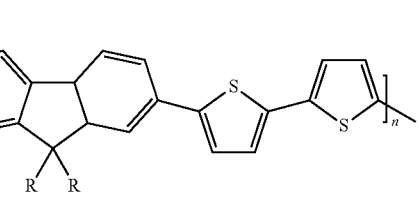
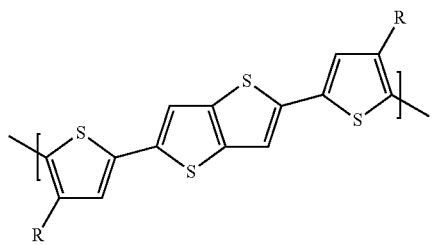

wherein n is an integer from 2 to 10,000, and R, R', $R_1$, $R_2$, X, and Y are each independently selected as hydrogen, $C_1$-$C_{40}$ alkyl, $C_1$-$C_{40}$ alkenyl, $C_1$-$C_{40}$ alkynl, $C_1$-$C_{40}$ alkoxy, $C_1$-$C_{40}$ cycloalkyl, $C_1$-$C_{40}$ aryl, $C_1$-$C_{40}$ heteroaryl, $C_1$-$C_{40}$ heterocycloalkyl, $C_1$-$C_{40}$ conjugated group, any of which may be optionally substituted, or halo.

16. The device of claim 1, wherein the collector layer comprises Al, Au, Ag, Pt, Cu, stainless steel, oxides thereof, alloys thereof or combinations thereof.

17. The device of claim 1, wherein the emitter layer comprises at least one of: a transparent conductive oxide, an organic polymer, or a combination thereof.

18. The device of claim 2, wherein each of the openings has a length along its longest dimension of from 200 nm to 500 nm.

19. The device of claim 1, further comprising a tube configured to remove moisture disposed between the outlet and the vertical gas sensor.

* * * * *

UNITED STATES PATENT AND TRADEMARK OFFICE
CERTIFICATE OF CORRECTION

PATENT NO. : 12,138,070 B2
APPLICATION NO. : 17/389765
DATED : November 12, 2024
INVENTOR(S) : Chen et al.

Page 1 of 5

It is certified that error appears in the above-identified patent and that said Letters Patent is hereby corrected as shown below:

In the Claims

Claim 6, Column 57, around Lines 47-59, delete:

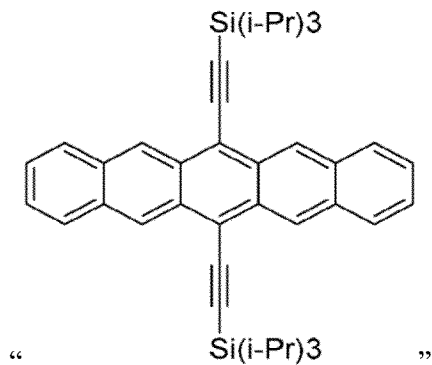

" "

And insert:

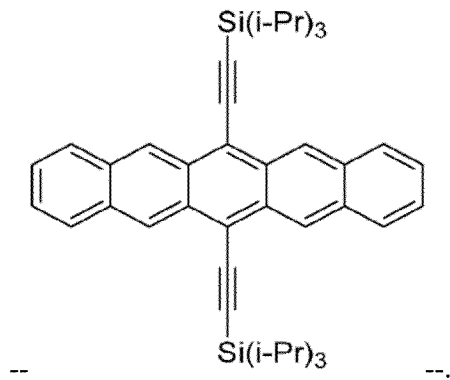

-- --.

Signed and Sealed this
Thirtieth Day of December, 2025

John A. Squires
*Director of the United States Patent and Trademark Office*

Claim 6, Column 60, around Lines 35-40, delete:
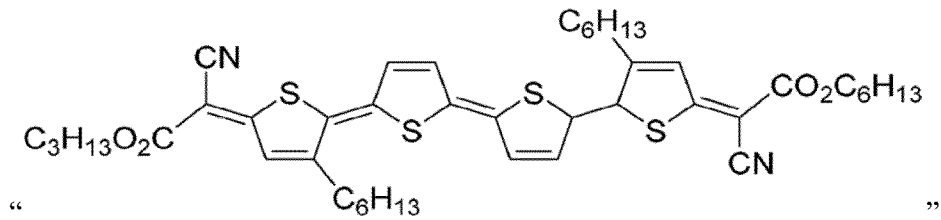
" "
And insert:
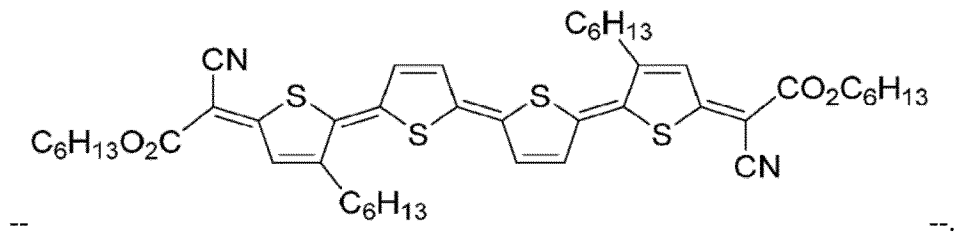
-- --.
Claim 15, Column 67, around Lines 10-20, delete:
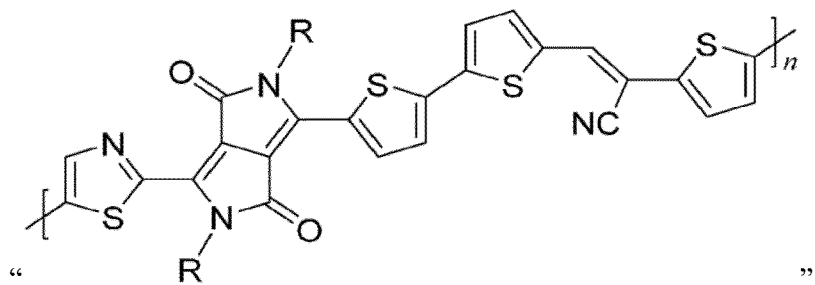
" "
And insert:
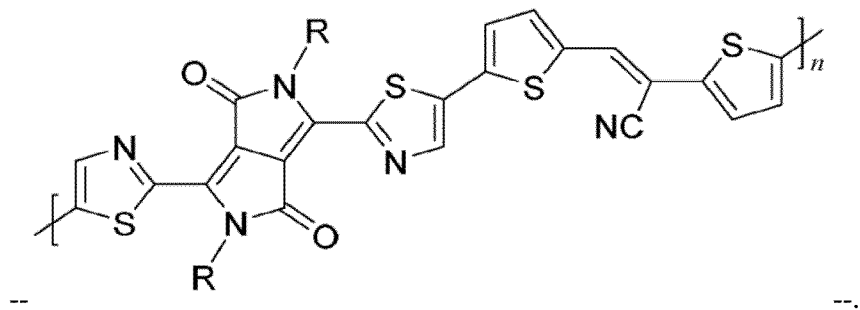
-- --.

CERTIFICATE OF CORRECTION (continued)
U.S. Pat. No. 12,138,070 B2

Claim 15, Column 69, around Lines 55-65, delete:

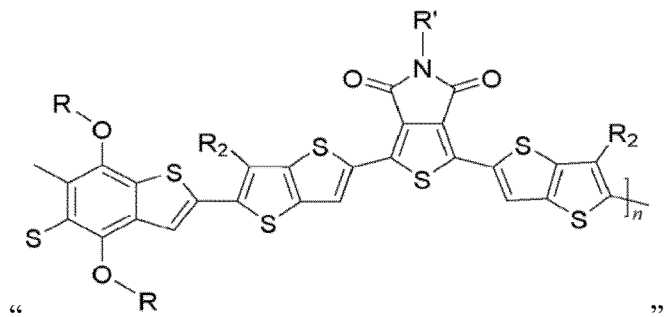

" "

And insert:

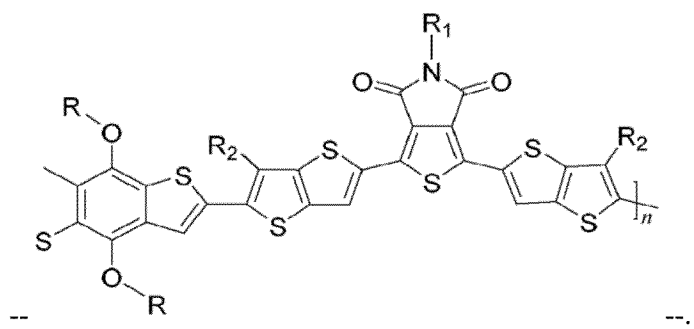

-- --.

Claim 15, Column 71, around Lines 15-20, delete:

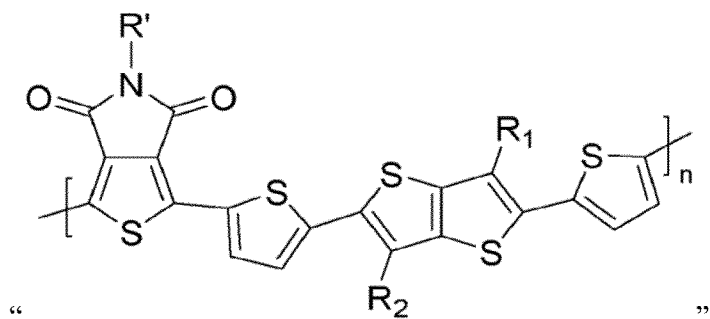

" "

And insert:

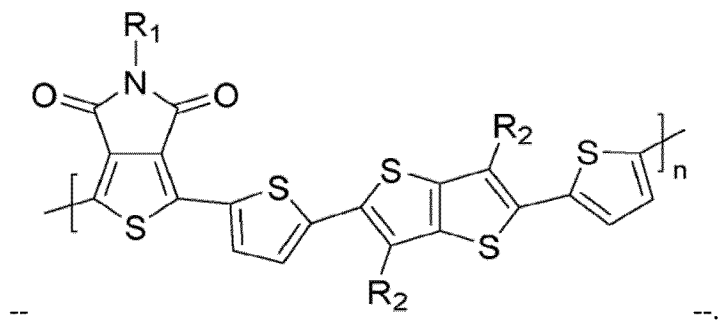

-- --.

Claim 15, Column 71, around Lines 30-40, delete:
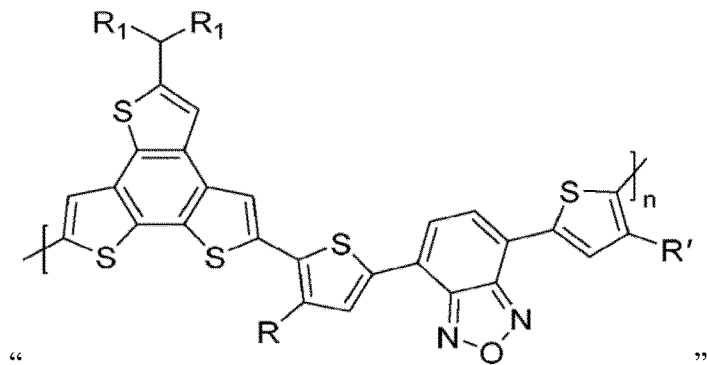
" "
And insert:
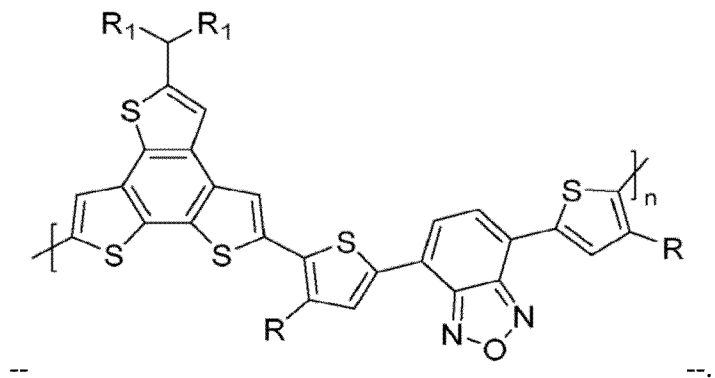
-- --.
Claim 15, Column 72, around Lines 5-15, delete:
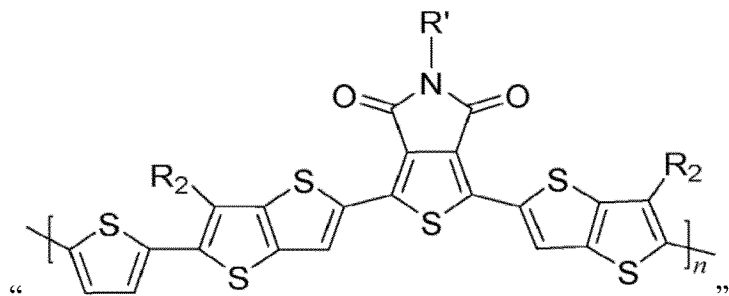
" "
And insert:
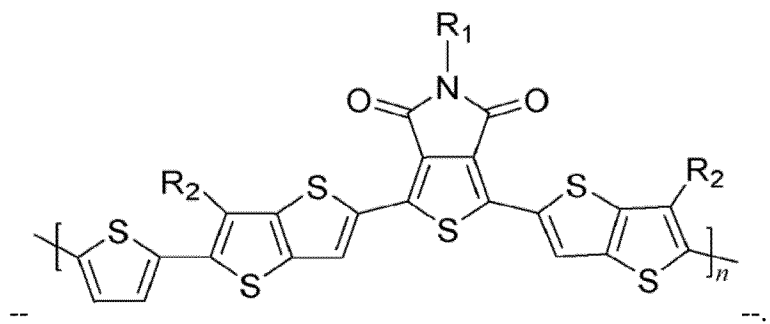
-- --.

CERTIFICATE OF CORRECTION (continued)
U.S. Pat. No. 12,138,070 B2

Claim 15, Column 75, around Lines 55-65, delete:

"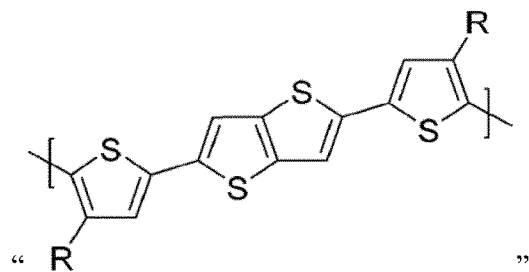"

And insert:

--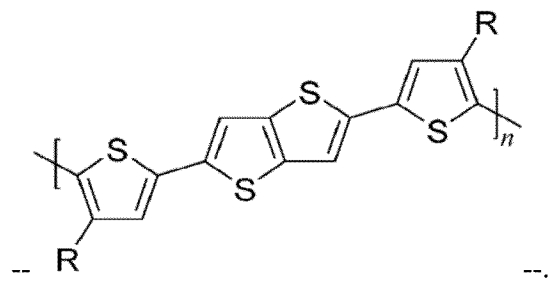--.